United States Patent

Onji et al.

[11] Patent Number: 5,382,379
[45] Date of Patent: Jan. 17, 1995

[54] CYCLOHEXANE DERIVATIVE

[75] Inventors: Yuichi Onji; Makoto Ushioda; Shuichi Matsui; Tomoyuki Kondo; Yasuyuki Goto, all of Chiba, Japan

[73] Assignee: Chisso Corporation, Ohsaka, Japan

[21] Appl. No.: 132,917

[22] Filed: Oct. 7, 1993

[30] Foreign Application Priority Data

Oct. 7, 1992 [JP] Japan ................... 4-268868

[51] Int. Cl.$^6$ ................ C09K 19/30; C07C 43/225; C07C 19/08
[52] U.S. Cl. ................ 252/299.63; 568/656; 568/661; 570/127
[58] Field of Search ............ 252/299.63, 299.01; 568/656, 661; 570/127, 182

[56] References Cited

U.S. PATENT DOCUMENTS

| | | | |
|---|---|---|---|
| 5,032,313 | 7/1991 | Goto et al. | 252/299.63 |
| 5,213,710 | 5/1993 | Reiffenrath et al. | 252/299.63 |
| 5,230,829 | 7/1993 | Bartmann et al. | 252/299.63 |

Primary Examiner—Shean Wu
Attorney, Agent, or Firm—Wenderoth, Lind & Ponack

[57] ABSTRACT

A novel liquid crystal material having an alkenyl group at the end of the molecule, and having a low viscosity is provided. When the compound is added to a display element it is able to reduce the threshold voltage of the resulting display element. The compound is expressed by the formula (I),

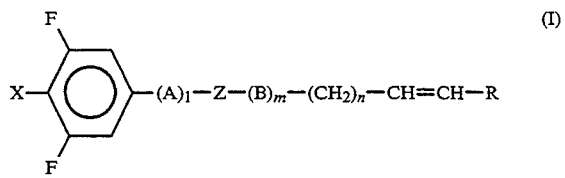

wherein X is a F atom, a trifluoromethyl group, a trifluoromethoxy group or a difluoromethoxy group, —A— is 1,4-cyclohexylene or 1,4-phenylene, —B— is 1,4-cyclohexylene, l is 0, 1 or 2, m is 0, 1 or 2, $1+m \geq 1$, Z is —CH$_2$CH$_2$— or single bond, n is an integer of 0 to 4, R is a H atom or a linear or branched alkyl group of 1-7C, and when R is an alkyl group, the double bond has a trans-configuration. The compounds of the present invention are suitable as liquid crystal material for STN display element, and further are chemically stable; hence it is possible to prepare a composition having a superior multiplex characteristic and capable of effecting a low voltage drive.

9 Claims, No Drawings

CYCLOHEXANE DERIVATIVE

BACKGROUND OF THE INVENTION

1. Field of the Invention

This invention relates to a cyclohexane derivative useful as a liquid crystal material. More particularly, it relates to a liquid crystalline compound having an alkenyl group at the end of its molecule and a liquid crystal composition containing the compound.

2. Description of the Related Art

Display elements utilizing liquid crystals have been broadly used for watches, electronic calculators, etc. These liquid crystal display elements are those utilizing the optical anisotropy and the dielectric anisotropy of liquid crystal substances. Liquid crystal phases include nematic liquid crystal phase, smectic liquid crystal phase and cholesteric liquid crystal phase, and among the above phases liquid crystal display elements utilizing nematic liquid crystal phase have been most broadly and practically used. Such display elements include those of TN (twisted nematic) mode, DS (dynamic scattering) mode, guest-host mode, DAP mode, etc., corresponding to the electro-optic effect applied to liquid crystal display, and as the liquid crystal substances utilized for the respective display elements, those exhibiting liquid crystal phases within a temperature range as broad as possible in the natural state are preferred. A large number of liquid crystal compounds have already been known, but at present, there is no single liquid crystal substance satisfying such conditions, but several kinds of liquid crystal substances or non-liquid crystal compounds have been mixed to be practically used. These substances are required to be stable to moisture, light, heat, air, etc. In particular, recently, there has been an increasing importance of substances having a low optical anisotropy, as a material for liquid crystal display element for active matrix mode represented by thin film transistor (TFT) mode. Further, it has been required for the liquid crystal material that its compatibility with a number of already existing liquid crystal materials is as large as possible at low temperatures.

The following compounds have so far been known as compounds similar to those of the present invention:

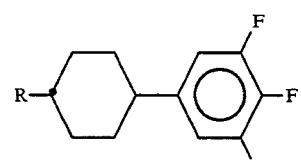

(Japanese patent application laid-open No. Hei 2-233626)

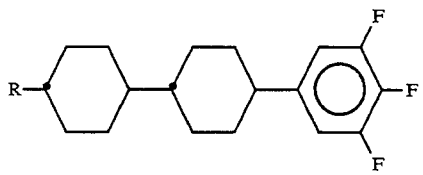

(Japanese patent application laid-open No. Hei 2-233626)

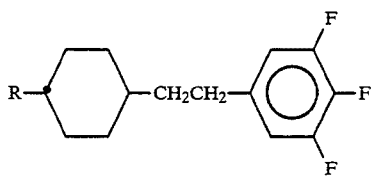

(Japanese patent application laid-open No. Hei 2-233626)

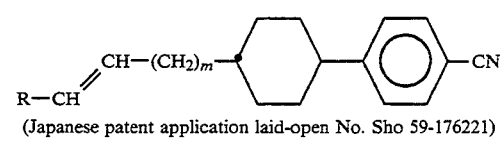

(Japanese patent application laid-open No. Sho 59-176221)

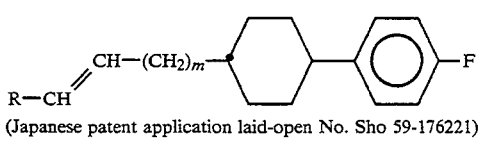

(Japanese patent application laid-open No. Sho 59-176221)

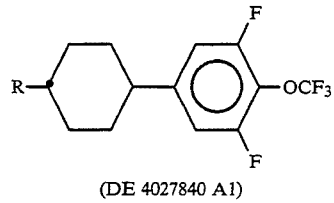

(DE 4027840 A1)

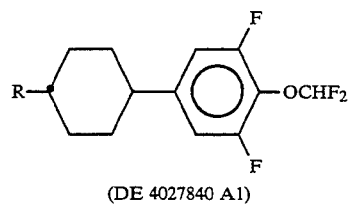

(DE 4027840 A1)

These compounds, particularly (I), (II), (III), (VI) and (VII), have been reported to have a large dielectric anisotropy value ($\Delta\epsilon$) and a low viscosity and exhibit an effect of lowering the threshold voltage without raising the viscosity. However, according to research of the present inventors, it has been found that the $\Delta\epsilon$ value is comparatively small and the threshold voltage cannot be sufficiently lowered.

SUMMARY OF THE INVENTION

The object of the present invention is to provide a cyclohexane derivative as a liquid crystal compound which has a low viscosity and can sufficiently lower the threshold voltage.

The present inventors have conducted extensive research in order to solve the above mentioned problems, and as a result, have found a compound having a novel structure and having improved characteristics over known liquid crystal compounds, and have completed the present invention.

The cyclohexane derivative of the present invention is a cyclohexane derivative expressed by the formula (I)

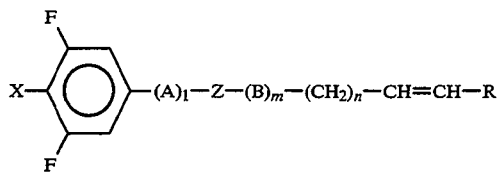

(I)

wherein X represents a fluorine atom, a trifluoromethyl group, trifluoromethoxy group or difluoromethoxy group, —A— represents 1,4-cyclohexylene or 1,4-phenylene, —B— represents 1,4-cyclohexylene, 1 represents 0, 1 or 2, m represents 0, 1 or 2, and $1+m \geq 1$, Z represents —CH$_2$CH$_2$— or a single bond, n represents an integer of 0 to 4, R represents a hydrogen atom or a linear or branched alkyl group of 1 to 7 carbon atoms, and when R represents an alkyl group, the double bond has a trans-configuration, and a liquid crystalline mixture containing at least one of the cyclohexane derivatives.

DETAILED DESCRIPTION OF PREFERRED EMBODIMENTS

Compounds having an alkenyl substituent group, so far reported, have a higher elastic constant ratio ($K_{33}/K_{11}$) than those of compounds having a normal alkyl substituent group, as reported in various papers, and hence they are suitable as a liquid crystal material for STN display elements.

The characteristic of the liquid crystal compound provided by the present invention, surprisingly enough, is that it has a lower elastic constant ratio ($K_{33}/K_{11}$) than those of compounds having a normal alkyl substituent group, in spite of having an alkenyl substituent group. Materials having a low $K_{33}/K_{11}$ are steep in the electro-optic characteristic of TN mode, and exhibit a superior multiplex characteristic.

This fact is known for example by the following articles:

a) J. Nehring, advance in Liquid Crystal Research and Applications (ed. L. Bata)., P1155. Pergamon Press
b) G. Baur, The Physics and Chemistry of Liquid Crystal Devices (ed. G. J. Sprokel)., P61, Plenum (1980 ).
c) Y. Takahashi, T. Uchida and M. Wada, Mol. Cryst. Liq. Cryst., 66, 171 (1981).

Further, since the compound of the present invention is chemically stable, it is possible to prepare a composition having a superior multiplex characteristic and capable of effecting a low voltage drive by using the compound of the present invention.

As the compound of the formula (I), compounds expressed by the formulas Ia to Ie can be exemplified (the definitions of the respective symbols are the same as those in the formula (I)).

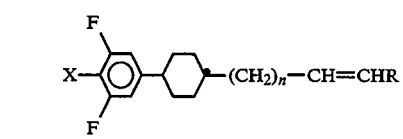
(Ia)

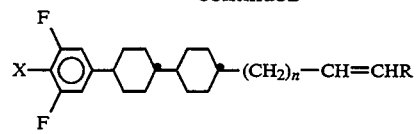
(Ib)

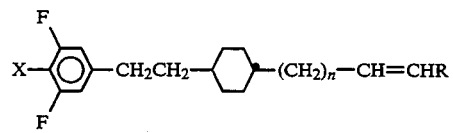
(Ic)

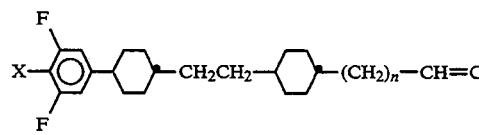
(Id)

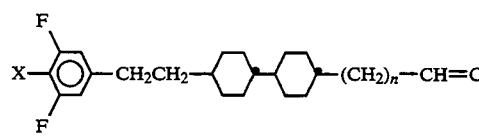
(Ie)

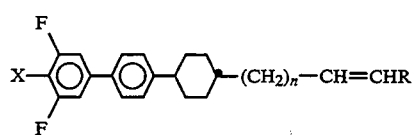
(If)

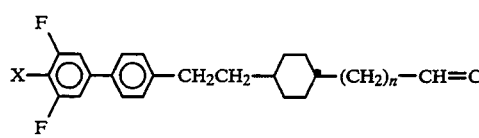
(Ig)

Particularly preferable compound among those of the respective formulas will be illustrated below.

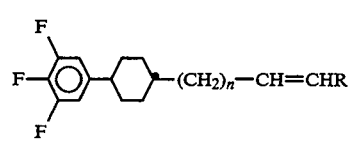
(Iaa)

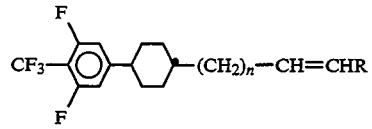
(Iab)

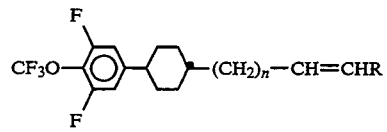
(Iac)

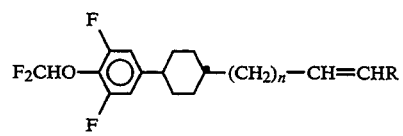
(Iad)

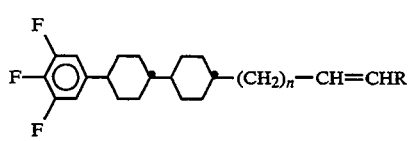
(Iba)

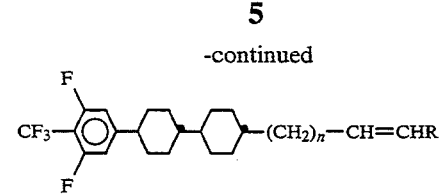 (Ibb)
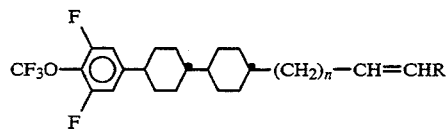 (Ibc)
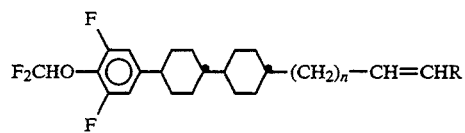 (Ibd)
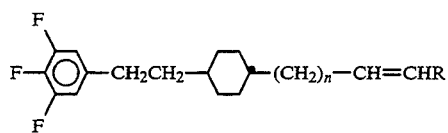 (Ica)
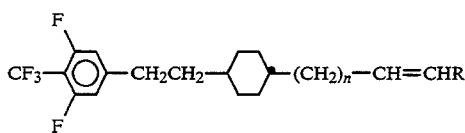 (Icb)
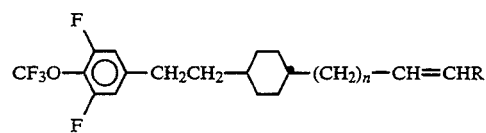 (Icc)
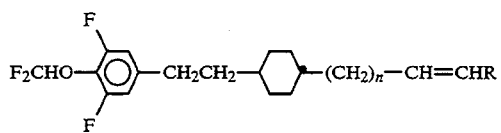 (Icd)
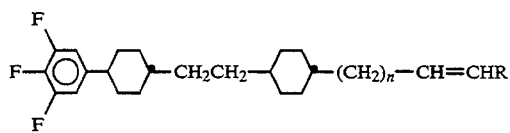 (Ida)
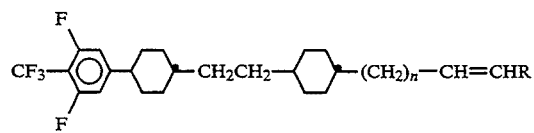 (Idb)
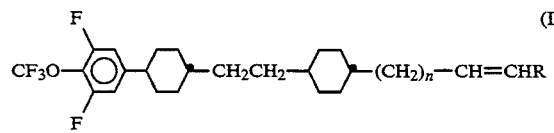 (Idc)
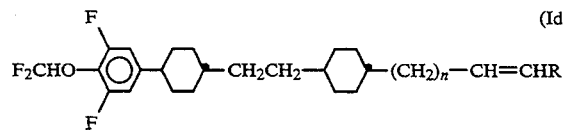 (Idd)
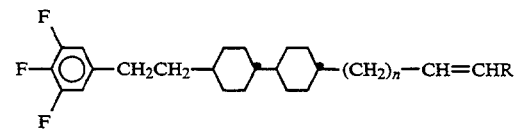 (Iea)
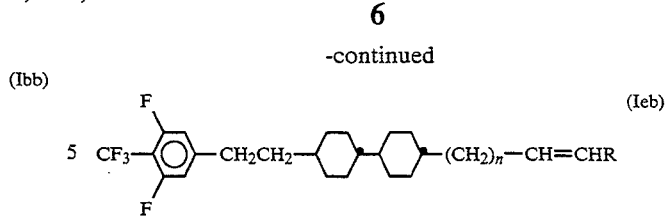 (Ieb)
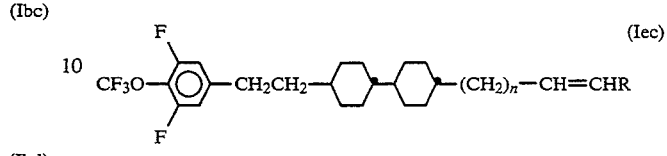 (Iec)
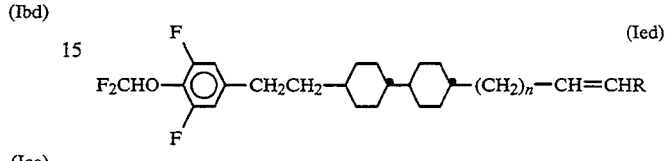 (Ied)
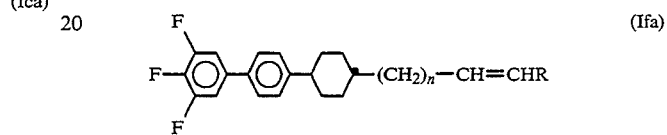 (Ifa)
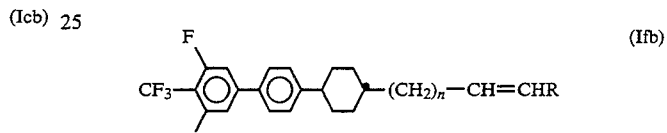 (Ifb)
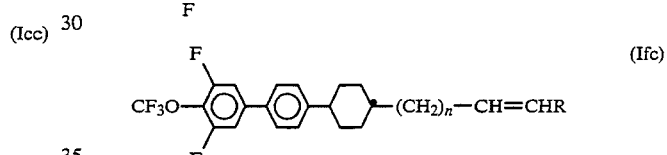 (Ifc)
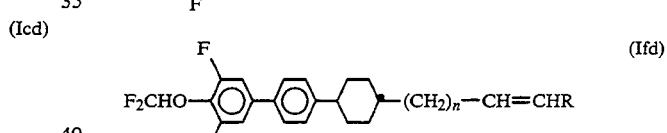 (Ifd)
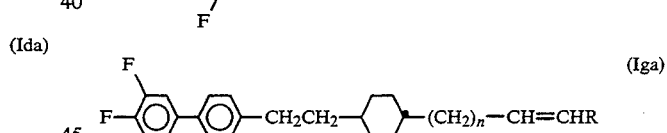 (Iga)
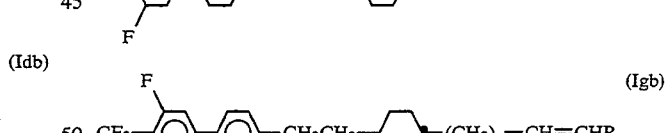 (Igb)
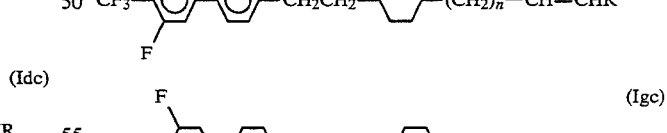 (Igc)
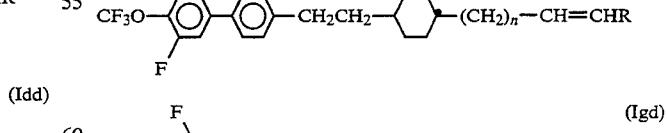 (Igd)
Compounds of the formula (I) wherein R represents an alkyl group, form a trans-configuration in the aspect of the steric structure directed to the double bond having R bonded thereto. The alkyl group of R is preferably a linear alkyl group of 1 to 7 carbon atoms, more preferably a methyl group, ethyl group, propyl group, butyl group and pentyl group.

The liquid crystal composition provided by the present invention is a liquid crystal dielectric comprising a component (A) containing at least one of the compounds expressed by the formula (I) and further, a component (B) containing at least one of compounds having a high dielectric anisotropy of preferably $\Delta\epsilon \geq 5$, a component (C) containing at least one of compounds having a low dielectric anisotropy of $|\Delta\epsilon| < 5$ and a component (D) containing at least one of compounds having a clearing point exceeding 80° C., and further, if required, another component (E).

Compounds particularly preferred as the component (B) will be shown below.

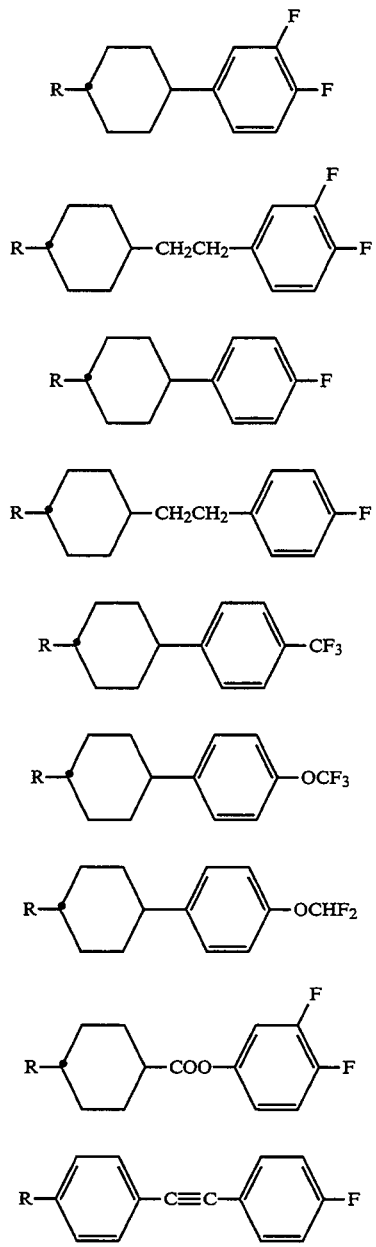

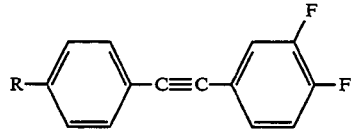

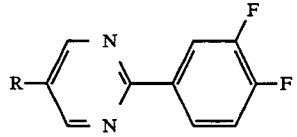

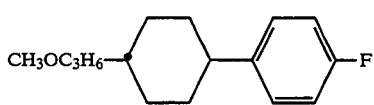

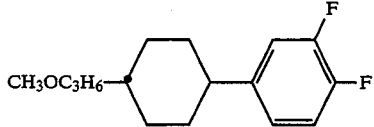

In tile above formulas, R represents an alkyl group or an alkenyl group of 1 to 10 carbon atoms, and one carbon atom or two non-adjacent carbon atoms of the groups may be replaced by an oxygen atom.

Compounds particularly preferred as tile component (C) will be shown below.

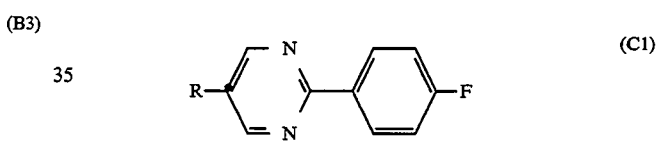

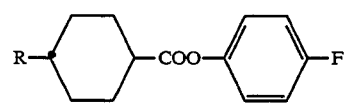

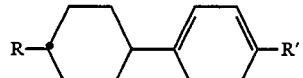

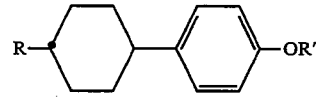

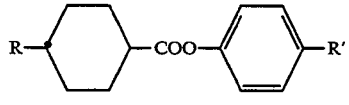

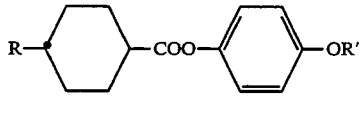

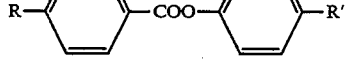

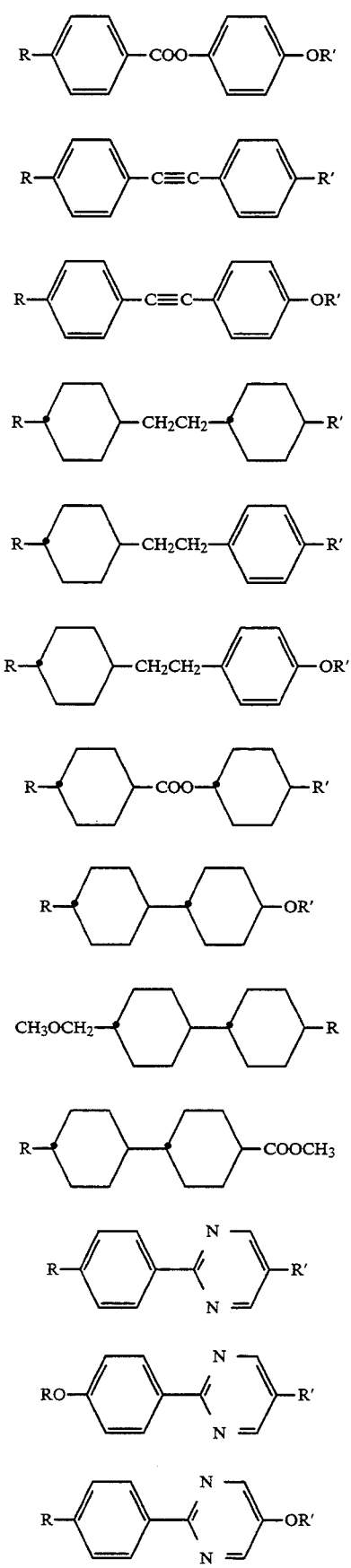
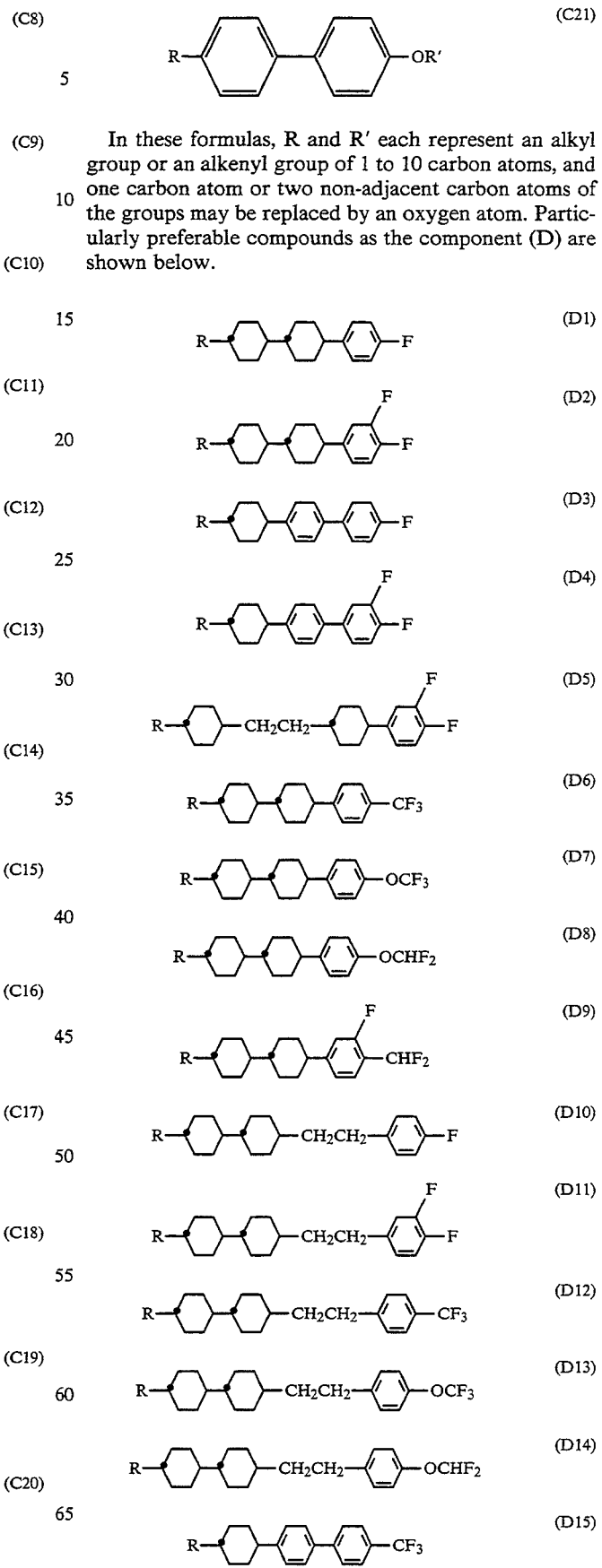
In these formulas, R and R' each represent an alkyl group or an alkenyl group of 1 to 10 carbon atoms, and one carbon atom or two non-adjacent carbon atoms of the groups may be replaced by an oxygen atom. Particularly preferable compounds as the component (D) are shown below.

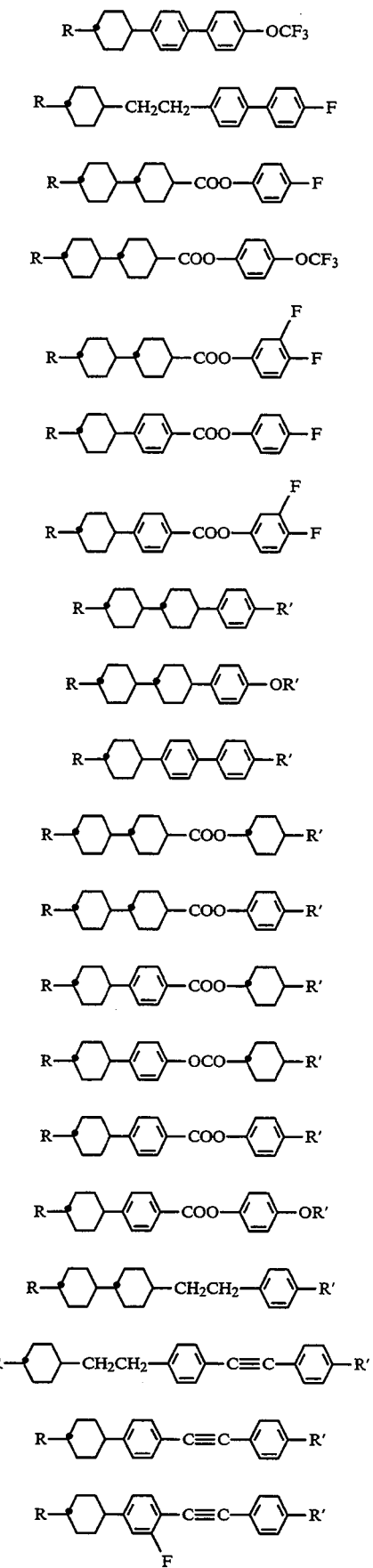
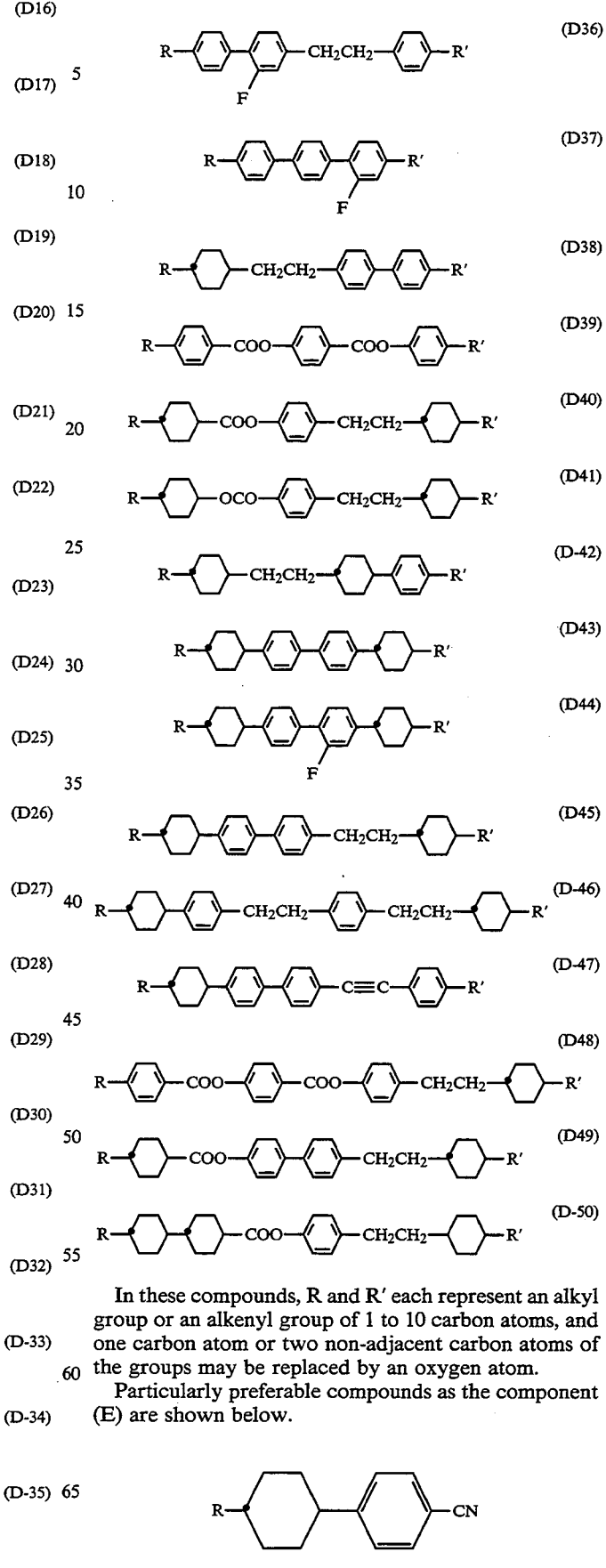
In these compounds, R and R' each represent an alkyl group or an alkenyl group of 1 to 10 carbon atoms, and one carbon atom or two non-adjacent carbon atoms of the groups may be replaced by an oxygen atom.
Particularly preferable compounds as the component (E) are shown below.

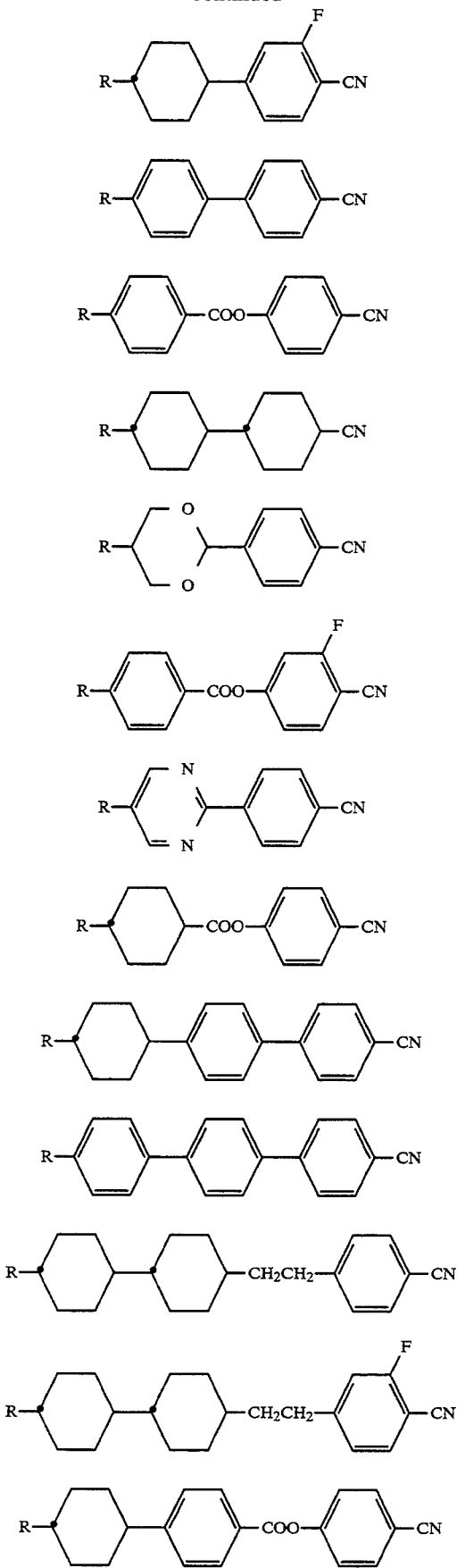

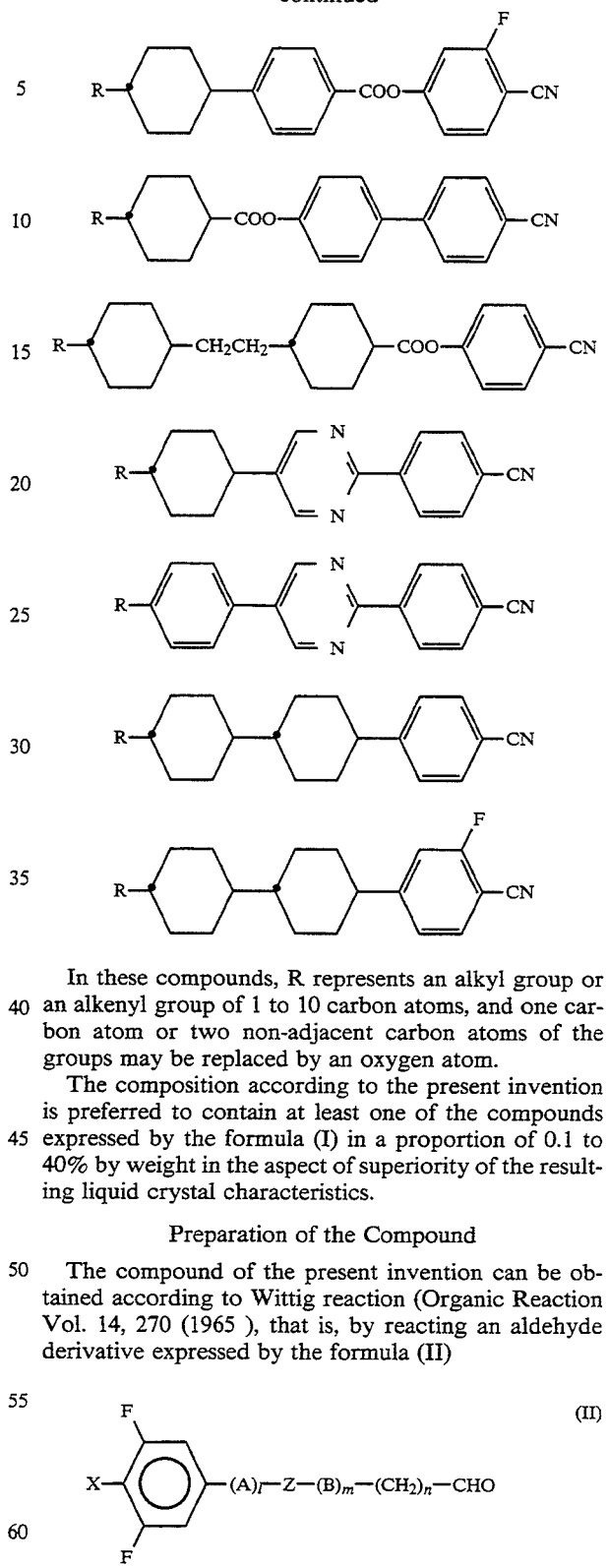

In these compounds, R represents an alkyl group or an alkenyl group of 1 to 10 carbon atoms, and one carbon atom or two non-adjacent carbon atoms of the groups may be replaced by an oxygen atom.

The composition according to the present invention is preferred to contain at least one of the compounds expressed by the formula (I) in a proportion of 0.1 to 40% by weight in the aspect of superiority of the resulting liquid crystal characteristics.

Preparation of the Compound

The compound of the present invention can be obtained according to Wittig reaction (Organic Reaction Vol. 14, 270 (1965)), that is, by reacting an aldehyde derivative expressed by the formula (II)

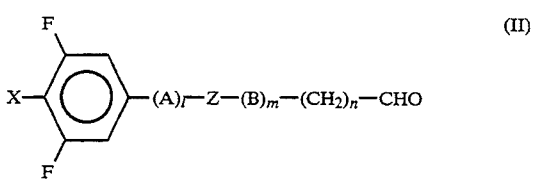

(II)

wherein X represents a fluorineatom, trifluoromethyl group, trifluoromethoxy group or difluoromethoxy group, —A— represents 1,4-cyclohexylene or 1,4-phenylene, —B— represents 1,4-cyclohexylene, 1 represents 0, 1 or 2, m represents 0, 1 or 2, and $l+m \geq 1$, Z represents —CH$_2$CH$_2$— or a single bond and n represents an integer of 0 to 4, with a phosphorus ylide compound expressed by the formula (III)

$$R_3'P=CH-R \quad \text{(III)}$$

wherein R represents a hydrogen atom or a linear or branched alkyl group of 1 to 7 carbon atoms and R' represents an alkyl group, an aryl group or an aralkyl group.

The compound of the present invention formed by the reaction of the compound of the formula (II) with that of the formula (III) is generally obtained in the form of a mixture of stereoisomers thereof, but the mixture can be separated for example according to a column chromatography. Further, if necessary, the mixture can be converted into the compound of the present invention according to a known method. Namely, by brominating the mixture with triphenylphosphinebromine and reducing the resulting halogenated compound, it is possible to convert to the mixture containing the compound of the present invention in a superior proportion.

In the process for producing the compound of the present invention, the reaction of the compound expressed by the formula (II) with that expressed by the formula (III) can be carried out according to a known method. For example, it is possible to use a compound (III) obtained by reacting the corresponding phosphonium compound with, as a preferable base, potassium t-butoxide, sodium methoxide, lithium diisopropylamide n-butyl lithium sodium hydride, pyridine, triethylamine or the like. This reaction and the succeeding reaction with the compound (II) is generally carried out in an organic solvent. As the solvent usable in the present reaction, those which do not hinder the reaction may be sufficient. For example, diethyl ether, tetrahydrofuran, dioxane, benzene, toluene, hexane, methylene chloride, chloroform, dimethylsulfoxide, dimethylformamide, etc. are preferable, and they can be used as a single solvent or a mixed solvent. The reaction temperature can be chosen from among the range of $-50°$ C. to the boiling point of the solvent used. The reaction is preferably carried out at $-30°$ C. to room temperature, but when the raw material concentration in the reaction mixture is high, the reaction should be carried out at $-30°$ C. to $0°$ C.

The compound expressed by the formula (II) as a starting substance for preparing the compound of the present invention can be prepared according to various methods represented by the following (1) to (5):

(1)
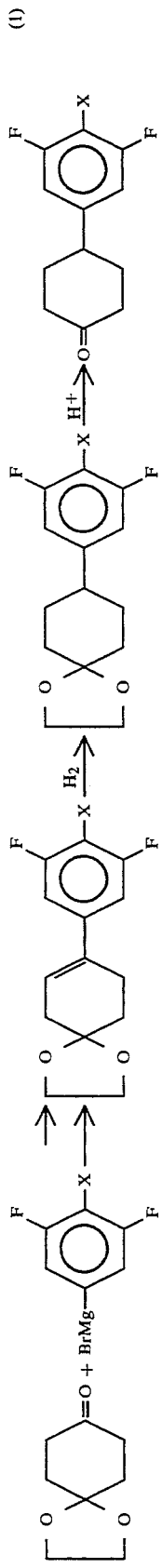
(2)
(3)
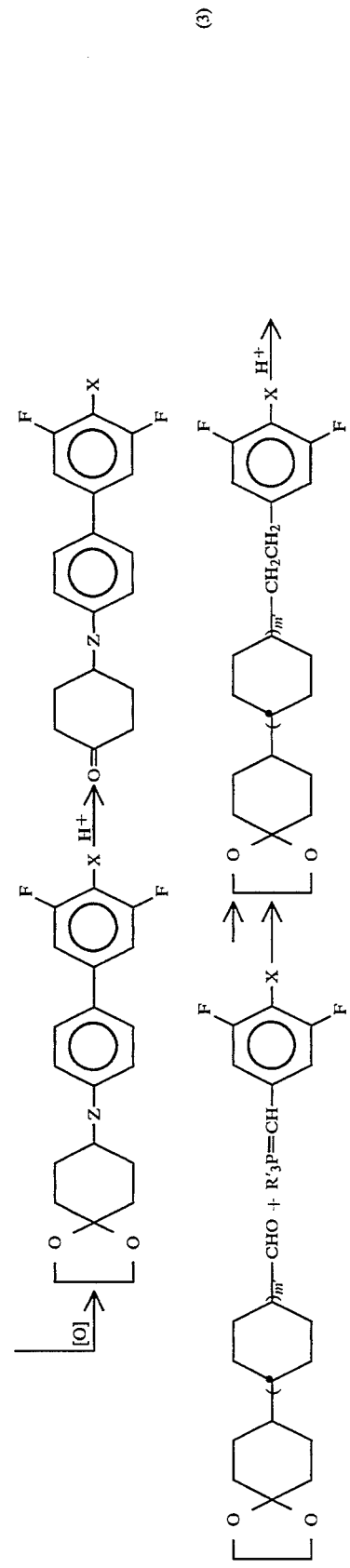
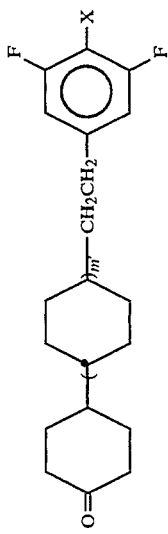

-continued
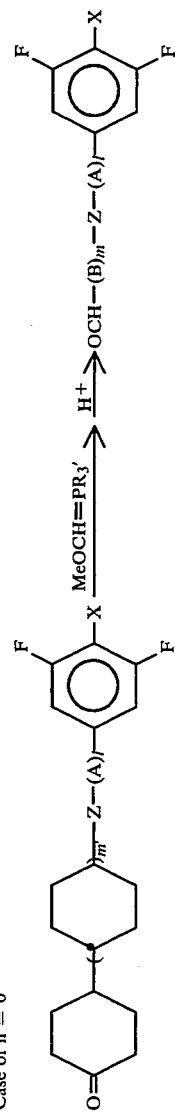
(4)
Case of n = 0
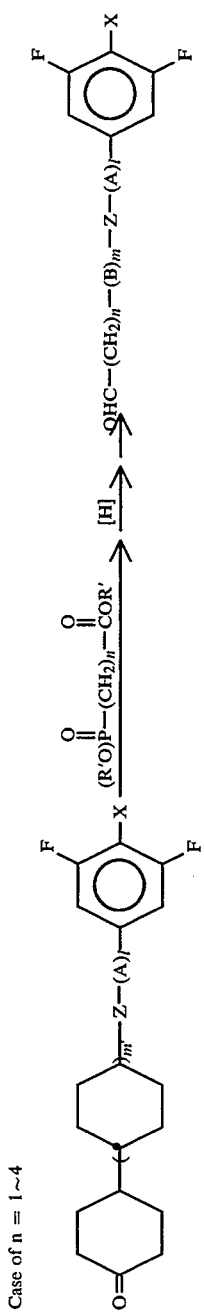
(5)-1
Case of n = 1~4
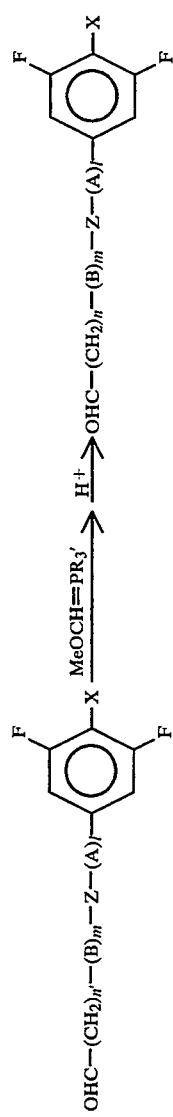
(5)-2

In these formulas, R is as defined above, X represents a fluorine atom, trifluoromethyl group, trifluoromethoxy group or difluoromethoxy group, 1 represents 0, 1 or 2, m represents 0, 1 or 2, and $1+m \geq 1$, —Z— represents —CH$_2$CH$_2$— or a single bond, n represents an integer of 1 to 4, n' represents n−1, and m' represents 0 or 1.

EXAMPLES

The compound of the present invention will be described in more detail by way of Examples, but it should not be construed to be limited thereto.

Example 1

Preparation of 5-(4'-trans-(3'',4'',5''-trifluorophenyl)-cyclohexyl)-2E-pentene (Compound No. 1)

(1) Mg (17.1 g) was suspended in THF (100 ml) in a nitrogen gas stream, followed by dropwise adding a solution of 3,4,5-trifluorobromobenzene (162 g) dissolved in THF (400 ml) to the suspension, stirring the mixture at room temperature for one hour, dropwise adding a solution of 1,4-cyclohexane-dionemonoethylene ketal (100 g) dissolved in tetrahydrofuran (THF) (400 ml), stirring the mixture at room temperature for one hour, adding a saturated aqueous solution of NH$_4$Cl (1 l) after completion of the reaction, extracting with ethyl acetate (1l), drying the organic layer over anhydrous MgSO$_4$ and distilling off the solvent under reduced pressure, to obtain 1, 1-ethylenedioxy-4-hydroxy-4-(3',4',5'-trifluorophenyl)cyclohexane (166 2 g).

(2) 1,1-Ethylenedioxy-4-hydroxy-4-(3',4',5'-trifluorophenyl)cyclohexane (166.2 g) was dissolved in toluene (500 ml), followed by adding p-toluenesulfonic acidmonohydrate (20 g) into the solution, stirring the mixture under reflux for one hour, washing the reaction solution with water (500 ml), drying the organic layer over anhydrous magnesium sulfate, and distilling off the solvent under reduced pressure, to obtain 1,1-ethylenedioxy-4-(3',4',5'-trifluorophenyl)-3-cyclohexene (102.6 g).

(3) 1,1-Ethylenedioxy-4-(3,4',5'-trifluorophenyl)-3-cyclohexen (100 g) was dissolved in ethanol (1 l), followed by adding Pd/C (5%) (40 g), stirring the mixture in a hydrogen gas atmosphere to carry out a catalytic reduction, filtering off the catalyst after the reaction, and distilling off the organic layer under reduced pressure, to obtain 1,1-ethylenedioxy4-(3',4',5'-trifluorophenyl)-cyclohexane (95 g).

(4) Formic acid (82.7 g) and toluene (20 ml) were added to 1,1-ethylenedioxy-4-(3',4', 5'-trifluorophenyl)cyclohexane (95.02 g), followed by heating the mixture under reflux with stirring for 2 hours, adding the reaction solution to water (500 ml), extracting with ethyl acetate (1 l), drying the organic layer over anhydrous magnesium sulfate, distilling off the solvent under reduced pressure, and recrystallizing from ethanol, to obtain 4-(3',4',5'-trifluorophenyl)cyclohexanone (63.1 g). m.p. 123.5° C.

(5) A suspension of 2-(1',3'-dioxan-2'-yl)ethyltriphenylphosphonium bromide (48.6 g) in THF (250 ml) was cooled down to 0° C. with stirring in a nitrogen gas stream, followed by adding potassium-t-butoxide (14.9 g) little by little, stirring the reaction solution at room temperature for one hour, dropwise adding a solution of 4 -(3',4',5'-trifluorophenyl)cyclohexanone (20 g) in THF (100 ml), raising the temperature of the reaction mixture up to room temperature, further stirring it for 2 hours, adding to water (500 ml) after completion of the reaction, extracting with ethyl acetate (1 l), drying the organic layer over anhydrous MgSO$_4$, concentrating under reduced pressure and subjecting to chromatography treatment on silica gel with ethyl acetate/heptane (1:5), to obtain 3',4',5'-trifluorophenyl-4-(2'-(1,3-dioxan-2-yl)ethylidene)cyclohexane (24.9 g).

(6) 3',4',5'-trifluorophenyl-4-(2'-(1'',3''-dioxan-2''-yl)ethylidene)cyclohexan (24.9 g) was dissolved in ethanol (200 ml), followed by adding Pd/C (5%) (15 g), stirring the mixture in a hydrogen gas atmosphere to carry out a catalytic reduction, filtering off the catalyst after completion of the reaction, distilling off the filtrate under reduced pressure and recrystallizing from ethanol according to a recrystallization procedure, to obtain 3+,4',5'-trifluorophenyl-4-(2'-(1'',3''-dioxan-2''-yl)ethyl)-cyclohexane (13.2 g).

(7) Formic acid (10 g) and toluene (2 ml) were added to 3+,4',5'-trifluorophenyl-4-(2'-(1'',3''-dioxan-2''-yl)ethyl)cyclohexan (13 g), followed by heating the mixture under reflux with stirring for 2 hours, adding the reaction solution to water (50 ml), extracting with ethyl acetate (100 ml), drying the organic layer over anhydrous magnesium sulfate and concentrating under reduced pressure, to obtain 3-(4'-(3'',4'',5''-trifluorophenyl)cyclohexyl)propionaldehyde (10.7 g).

(8) A suspension of ethyltriphenylphosphonium bromide (11.2 g) in THF (50 ml) was stirred in a nitrogen gas atmosphere, followed by cooling it down to 0° C., adding potassium-t-butoxide (4.2 g) little by little, agitating the reaction solution at room temperature for one hour, dropwise adding a solution of 3-(4'-(3'',4'',5''-trifluorophenyl)cyclohexyl)-propionaldehyde (67.8 g) in THF (20 ml), raising the reaction mixture up to room temperature, further stirring it for 2 hours, adding to water (50 ml) after completion of the reaction, extracting with ethyl acetate (100 ml), drying the organic layer over anhydrous magnesium sulfate, concentrating under reduced pressure, and carrying out chromatography treatment on silica gel with ethyl acetate/heptane (1:5), to obtain 5-(4'-(3'',4'',5''-trifluorophenyl)cyclohexyl-2-pentene (4.09 g).

(9) m-Chloroperbenzoic acid (7.7 g) and potassium carbonate (6.2 g) were fed into a solution of 5-(4'-(3'',4'',5''-trifluorophenyl)cyclohexyl-2-pentene (4.09 g) in methylene chloride (50 ml) to obtain a mixture, followed by stirring the mixture for 2 hours in an ice bath, adding water (50 ml), after completion of the reaction, extracting with methylene chloride (100 ml), drying the organic layer over anhydrous MgSO$_4$ and concentrating it under reduced pressure to obtain 5-(4'-(3'',4'',5''-trifluorophenyl)cyclohexyl) -2,3-epoxypentane (3.84 g).

(10) Dibromotriphenylphosphine (12.3 g) was fed into a suspension of 5-(4'-(3'',4'',5''-trifluorophenyl)cyclohexyl)-2,3-epoxypentane (3.84 g) in benzene (100 ml) to obtain a mixture, followed by heating the mixture under reflux with stirring for 2 hours, adding to water (100 ml) after completion of the reaction, extracting with ethyl acetate (100 ml), drying the organic layer over anhydrous MgSO$_4$, concentrating it under reduced pressure, and carrying out chromatography treatment on silica gel with ethyl acetate/heptane (1:5), to obtain 5-(4'-(3",4",5"-trifluorophenyl)cyclohexyl-2,3-dibromopentane (3.33 g).

(11) Zinc powder (3.2 g) was fed into a solution of 5-(4'-(3",4",5"-trifluorophenyl)cyclohexyl)-2,3-dibromopentane (3.33 g) in acetic acid (50 ml) to obtain a mixture, followed by stirring the mixture at room temperature over night, filtering off solids after completion of the reaction, adding the filtrate to water (50 ml), extracting with ethyl acetate (100 ml), drying the organic layer over anhydrous MgSO$_4$, concentrating under reduced pressure, carrying out chromatography treatment on silica gel with ethyl acetate/heptane (1:5), and recrystallizing from heptane, to obtain 5-(4'-(3",4",5"-trifluorophenyl) cyclohexyl)-2E-pentene (320 mg). m.p. 13.8°–16.9° C.

Example 2

Preparation of 4-trans-(3',4',5'-trifluorophenyl)cyclohexylethene (Compound No. 2)

(1) A suspension of methoxymethyltriphenylphosphonium chloride (36.4 g) in THF (200 ml) was stirred in a nitrogen gas stream, followed by adding potassium-t-butoxide (12 g) little by little, while cooling the suspension at 0° C., stirring the reaction solution at room temperature for one hour, dropwise adding a solution of 4-(3',4',5'-trifluorophenyl)cyclohexanone (20 g) in THF (100 ml), raising the temperature of the reaction mixture up to room temperature, further stirring for 2 hours, adding to water (100 ml) after completion of the reaction, extracting with ethyl acetate (200 ml), drying the organic layer over anhydrous MgSO$_4$, concentrating it under reduced pressure, and carrying out chromatography treatment on silica gel with ethyl acetate/heptane (1:5), to obtain 4-(3',4',5'-trifluorophenyl)methoxymethylenecyclohexane (18.25 g).

(2) THF (40 ml) and 2N hydrochloric acid (20 ml) were added to 4-(3',4',5'-trifluorophenyl)methoxymethylenecyclohexane (14.5 g), followed by heating the mixture under reflux with stirring for 2 hours, adding to water (200 ml) after completion of the reaction, extracting with ethyl acetate (500 ml), drying the organic layer over anhydrous MgSO$_4$, and concentrating under reduced pressure, to obtain 4-(3',4',5'-trifluorophenyl)cyclohexanecarbaldehyde (6.5 g).

(3) A suspension of methyltriphenylphosphonium bromide (2.7) in THF (20 ml) was stirred in a nitrogen gas stream, followed by adding potassium-t-butoxide (1.1 g) little by little, while cooling the suspension at 0° C., stirring the reaction solution at room temperature for one hour, dropwise adding a solution of 4-(3',4',5'-trifluorophenyl)cyclohexanecarbaldehyde (1.5 g) in THF (5 ml), raising the temperature of the reaction mixture up to room temperature, further stirring for 2 hours, adding to water (50 ml) after completion of the reaction, extracting with ethyl acetate (100 ml), drying the organic layer over anhydrous MgSO$_4$, concentrating under reduced pressure, carrying out chromatography treatment on silica gel with ethyl acetate/heptane (1:5), and recrystallizing from heptane, to obtain 4-trans-(3',4',5'-trifluorophenyl)cyclohexylethene (1.05 g). m.p. 20.3°–21.3° C.

Example 3

Preparation of 4-trans-(3',5'-difluoro-4'-trifluoromethylphenyl)cyclohexylethene (Compound No. 3)

(1) Mg (3.4 g) was suspended in THF (20 ml) in a nitrogen gas stream, followed by dropwise adding a solution of 3,5-difluoro-4-trifluoromethylbromobenzene (40 g) in THF (100 ml) to the suspension, stirring the mixture at room temperature for one hour, dropwise adding a solution of 1,4-cyclohexanedionemonoethylene ketal (20 g) in THF (100 ml), stirring the mixture at room temperature for one adding a saturated aqueous solution of NH$_4$Cl (200 ml) after completion of the reaction, extracting with ethyl acetate (500 ml), drying the organic layer over anhydrous MgSO$_4$, and distilling off the solvent under reduced pressure, to obtain 1,1-ethylenedioxy-4-hydroxy-4-(3',5'-difluoro-4'-trifluoromethylphenyl)cyclohexane (23 g).

(2) 1,1-Ethylenedioxy-4-hydroxy-4-(3',5'-difluoro-4'-trifluoromethylphenyl)cyclohexane (23 g) was dissolved in toluene (200 ml), followed by adding p-toluenesulfonic acidmonohydrate (5 g) to the solution, stirring the mixture under reflux for one hour, allowing the mixture to cool down, washing the reaction solution with water (200 ml), drying the organic layer over anhydrous MgSO$_4$, and distilling off the solvent, to obtain 1,1-ethylenedioxy-4-(3',5'-difluoro-4'-trifluoromethylphenyl)-3-cyclohexene (17.3 g).

(3) 1,1-Ethylenedioxy-4-(3',5'-difluoro-4'-trifluoromethylphenyl)-3-cyclohexene (17.3 g) was dissolved in ethanol (200 ml), followed by adding Pd/C (5%) (5 g), carrying out a catalytic reduction with stirring in a hydrogen gas atmosphere, filtering off the catalyst after completion of the reaction, and distilling off the organic layer under reduced pressure, to obtain 1,1-ethylenedioxy-4-(3',5'-difluoro-4'-trifluoromethylphenyl)cyclohexane (15.7 g).

(4) Formic acid (11.3 g) and toluene (5 ml) were added to 1,1-ethylenedioxy-4-(3',5'-difluoro-4'-trifluoromethylphenyl)cyclohexane (15.7 g), followed by heating the mixture under reflux with stirring for 2 hours, adding the reaction solution to water (50 ml), extracting with ethyl acetate (100 ml), drying the organic layer over anhydrous MgSO$_4$, and distilling off the solvent under reduced pressure, to obtain 4-(3',5'-difluoro-4'-trifluoromethylphenyl)cyclohexanone (12.0 g).

(5) A suspension of methoxymethyltriphenylphosphonium chloride (7 g) in THF (20 ml) was stirred in a nitrogen gas stream, followed by adding potassium-t-butoxide (2.9 g) little by little, while cooling the suspension at 0° C., stirring the reaction solution at room temperature for one hour, dropwise adding a solution of 4-(3',5'-difluoro-4'-trifluoromethylphenyl)cyclohexanone (4.7 g) in THF (30 ml), raising the temperature of the reaction mixture up to room temperature, further stirring it for 2 hours, adding to water (100 ml) after completion of the reaction, extracting with ethyl acetate (200 ml), drying the organic layer over anhydrous MgSO$_4$, concentrating it under reduced pressure, and carrying out chromatography treatment on silica gel, with ethyl acetate/heptane (1:5), to obtain 4-(3',5'-difluoro-4'-trifluoromethylphenyl)methoxymethylenecyclohexane (2.06 g).

(6) THF (10 ml) and 2N hydrochloric acid (10 ml) were added to 4-(3',5'-difluoro-4'-trifluoromethylphenyl)methoxymethylenecyclohexane (2.06 g), followed by heating the mixture under reflux with stirring for 2 hours, adding to water (20 ml) after completion of the reaction, extracting with ethyl acetate (50 ml), drying the organic layer over anhydrous MgSO$_4$, and concentrating under reduced pressure, to obtain 4-(3',5'-difluoro-4'-trifluoromethylphenyl)cyclohexanecarbaldehyde (1.99 g).

(7) A suspension of methyltriphenylphosphonium bromide (3 ) in THF (10 ml) was stirred in a nitrogen gas stream, followed by adding potassium-t-butoxide (1.2 g) little by little, while cooling the suspension at 0° C., stirring the reaction solution at room temperature for one hour, dropwise adding solution of 4-(3',5'-difluoro-4'-trifluoromethylphenyl)cyclohexanecarbaldehyde (1.99 g) in THF (5 ml), raising the temperature of the reaction mixture up to room temperature, further stirring for 2 hours, adding to water (20 ml) after completion of the reaction, extracting with ethyl acetate (50 ml), drying the organic layer over anhydrous MgSO$_4$, concentrating under reduced pressure, carrying out chromatography treatment on silica gel with ethyl acetate/heptane (1:5) and recrystallizing from heptane, to obtain 4-trans-(3',5'-difluoro-4'-trifluoromethylphenyl)cyclohexylethene (300 mg).

The following compounds are prepared according to the above-mentioned procedure:

Compound Nos.

4. 3-(4'-trans-(3",4",5"-trifluorophenyl)cyclohexyl)-2E-propene
5. 3-(4'-trans-(3",4",5"-trifluorophenyl)cyclohexyl)-1-propene
6. 4-(4'-trans-(3",4",5"-trifluorophenyl)cyclohexyl)-1-butene m.p. 16.8°–19.3° C.
7. 4-(4'-trans-(3",4",5"-trifluorophenyl)cyclohexyl)-2E-butene
8. 4-(4'-trans-(3",4",5"-trifluorophenyl)cyclohexyl)-3E-butene
9. 5-(4'-trans-(3",4",5"-trifluorophenyl)cyclohexyl)-1-pentene
10. 5-(4'-trans-(3",4",5"-trifluorophenyl)cyclohexyl)-3E-pentene
11. 5-(4'-trans-(3",4",5"-trifluorophenyl)cyclohexyl)-4E-pentene
12. 6-(4'-trans-(3",4",5"-trifluorophenyl)cyclohexyl)-1-hexene
13. 5-(4'-trans-(3",4",5"-trifluorophenyl)cyclohexyl)-2E-hexene
14. 6-(4'-trans-(3",4",5"-trifluorophenyl)cyclohexyl)-3E-hexene
15. 5-(4'-trans-(3",4",5"-trifluorophenyl)cyclohexyl)-4E-hexene
16. 7-(4'-trans-(3",4",5"-trifluorophenyl)cyclohexyl)-2E-heptene
17. 7-(4'-trans-(3",4",5"-trifluorophenyl)cyclohexyl)-3E-heptene
18. 7-(4'-trans-(3",4",5"-trifluorophenyl)cyclohexyl)-4E-heptene
19. 8-(4'-trans-(3",4",5"-trifluorophenyl)cyclohexyl)-3E-octene
20. 8-(4'-trans-(3",4",5"-trifluorophenyl)cyclohexyl)-4E-octene
21. 9-(4'-trans-(3",4",5"-trifluorophenyl)cyclohexyl)-4E-nonene
22. 3-(4'-trans-(3",5"-difluoro-4"-trifluoromethylphenyl)cyclohexyl)-2E-propene
23. 3-(4'-trans-(3",5"-difluoro-4"-trifluoromethylphenyl)cyclohexyl)-1-propene
24. 4-(4'-trans-(3",5"-difluoro-4"-trifluoromethylphenyl)cyclohexyl)-1-butene
25. 4-(4'-trans-(3",5"-difluoro-4"-trifluoromethylphenyl)cyclohexyl)-2E-butene
26. 4-(4'-trans-(3",5"-difluoro-4"-trifluoromethylphenyl)cyclohexyl)-3E-butene
27. 5-(4'-trans-(3",5"-difluoro-4"-trifluoromethylphenyl)cyclohexyl)-1-pentene
28. 5-(4'-trans-(3",5"-difluoro-4"-trifluorcmEthylphenyl)cyclohexyl)-2E-pentene
29. 5-(4'-trans-(3",5"-difluoro-4"-trifluoromethylphenyl)cyclohexyl)-3-pentene
30. 5-(4'-trans-(3",5"-difluoro-4"-trifluoromethylphenyl)cyclohexyl)-4E-pentene
31. 6-(4'-trans-(3",5"-difluoro-4"-trifluoromethylphenyl)cyclohexyl)-1-hexene
32. 6-(4'-trans-(3",5"-difluoro-4"-trifluoromethylphenyl)cyclohexyl)-2E-hexene
33. 6-(4'-trans-(3",5"-difluoro-4"-trifluoromethylphenyl)cyclohexyl)-3E-hexene
34. 6-(4'-trans-(3",5"-difluoro-4"-trifluoromethylphenyl)cyclohexyl)-4E-hexene
35. 7-(4'-trans-(3",5"-difluoro-4"-trifluoromethylphenyl)cyclohexyl)-2E-heptene
36. 7-(4'-trans-(3",5"-difluoro-4"-trifluoromethylphenyl)cyclohexyl)-3E-heptene
37. 7-(4'-trans-(3",5"-difluoro-4"-trifluoromethylphenyl)cyclohexyl)-4E-heptene
38. 8-(4'-trans-(3",5"-difluoro-4"-trifluoromethylphenyl)cyclohexyl)-3E-octene
39. 8-(4'-trans-(3",5"-difluoro-4"-trifluoromethylphenyl)cyclohexyl)-4E-octene
40. 9-(4'-trans-(3",5"-difluoro-4"-trifluoromethylphenyl)cyclohexyl)-4E-nonene
41. 2-(4'-trans-(3",5"-difluoro-4"-trifluoromethoxylphenyl)cyclohexyl) ethene
42. 3-(4'-trans-(3",5"-difluoro-4"-trifluoromethoxylphenyl)cyclohexyl)-2E-propene
43. 3-(4'-trans-(3",5"-difluoro-4"-trifluoromethoxylphenyl)cyclohexyl)-1-propene
44. 4-(4'-trans-(3",5"-difluoro-4"-trifluoromethoxylphenyl)cyclohexyl)-1-butene
45. 4-(4'-trans-(3",5"-difluoro-4"-trifluoromethoxylphenyl)cyclohexyl)-2E-butene
46. 4-(4'-trans-(3",5"-difluoro-4"-trifluoromethoxylphenyl)cyclohexyl)-3E-butene
47. 5-(4'-trans-(3",5"-difluoro-4"-trifluoromethoxylphenyl)cyclohexyl)-1-pentene
48. 5-(4'-trans-(3",5"-difluoro-4"-trifluoromethoxylphenyl)cyclohexyl)-2E-pentene
49. 5-(4'-trans-(3",5"-difluoro-4"-trifluoromethoxylphenyl)cyclohexyl)-3E-pentene
50. 5-(4'-trans-(3",5"-difluoro-4"-trifluoromethoxylphenyl)cyclohexyl)-4E-pentene
51. 6-(4'-trans-(3",5"-difluoro-4"-trifluoromethoxylphenyl)cyclohexyl)-1-hexene
52. 6-(4'-trans-(3",5"-difluoro-4"-trifluoromethoxylphenyl)cyclohexyl)-2E-hexene
53. 6-(4'-trans-(3",5"-difluoro-4"-trifluoromethoxylphenyl)cyclohexyl)-3E-hexene
54. 6-(4'-trans-(3",5"-difluoro-4"-trifluoromethoxylphenyl)cyclohexyl)-4E-hexene
55. 7-(4'-trans-(3",5"-difluoro-4"-trifluoromethoxylphenyl)cyclohexyl)-2E-heptene 56. 7-(4'-trans-(3",5"-difluoro-4"-trifluoromethoxyl-phenyl)cyclohexyl)-3E-heptene
57. 7-(4'-trans-(3",5"-difluoro-4"-trifluoromethoxyl-phenyl)cyclohexyl)-4E-heptene
58. 8-(4'-trans-(3",5"-difluoro-4"-trifluoromethoxyl-phenyl)cyclohexyl)-3E-octene
59. 8-(4'-trans-(3",5"-difluoro-4"-trifluoromethoxyl-phenyl)cyclohexyl)-4E-octene
60. 9-(4'-trans-(3",5"-difluoro-4"-trifluoromethoxyl-phenyl)cyclohexyl)-4E-nonene
61. 2-(4'-trans-(3",5"-difluoro-4"-difluoromethoxyl-phenyl)cyclohexyl)ethene
62. 3-(4'-trans-(3",5"-difluoro-4"-difluoromethoxyl-phenyl)cyclohexyl)-2E-propene
63. 3-(4'-trans-(3",5"-difluoro-4"-difluoromethoxyl-phenyl)cyclohexyl)-1-propene
64. 4-(4'-trans-(3",5"-difluoro-4"-difluoromethoxyl-phenyl)cyclohexyl)-1-butene
65. 4-(4'-trans-(3",5"-difluoro-4"-difluoromethoxyl-phenyl)cyclohexyl)-2E-butene
66. 4-(4'-trans-(3",5"-difluoro-4"-difluoromethoxyl-phenyl)cyclohexyl)-3E-butene
67. 5-(4'-trans-(3",5"-difluoro-4"-difluoromethoxyl-phenyl)cyclohexyl)-1-pentene
68. 5-(4'-trans-(3",5"-difluoro-4"-difluoromethoxyl-phenyl)cyclohexyl)-2E-pentene
69. 5-(4'-trans-(3",5"-difluoro-4"-difluoromethoxyl-phenyl)cyclohexyl)-3E-pentene
70. 5-(4'-trans-(3",5"-difluoro-4"-difluoromethoxyl-phenyl)cyclohexyl)-4E-pentene
71. 6-(4'-trans-(3",5"-difluoro-4"-difluoromethoxyl-phenyl)cyclohexyl)-1-hexene
72. 6-(4'-trans-(3",5"-difluoro-4"-difluoromethoxyl-phenyl)cyclohexyl)-2E-hexene
73. 6-(4'-trans-(3",5"-difluoro-4"-difluoromethoxyl-phenyl)cyclohexyl)-3E-hexene
74. 6-(4'-trans-(3",5"-difluoro-4"-difluoromethoxyl-phenyl)cyclohexyl)-4E-hexene
75. 7-(4'-trans-(3",5"-difluoro-4"-difluoromethoxyl-phenyl)cyclohexyl)-2E-heptene
76. 7-(4'-trans-(3",5"-difluoro-4"-difluoromethoxyl-phenyl)cyclohexyl)-3E-heptene
77. 7-(4'-trans-(3",5"-difluoro-4"-difluoromethoxyl-phenyl)cyclohexyl)-4E-heptene
78. 8-(4'-trans-(3",5"-difluoro-4"-difluoromethoxyl-phenyl)cyclohexyl)-3E-octene
79. 8-(4'-trans-(3",5"-difluoro-4"-difluoromethoxyl-phenyl)cyclohexyl)-4E-octene
80. 9-(4'-trans-(3",5"-difluoro-4"-difluoromethoxyl-phenyl)cyclohexyl)-4E-nonene.

Example

Preparation of 2-(4'-trans-(4"-trans-(3'",4'", 5'"-trifluorophenyl)cyclohexyl)cyclohexyl)ethene (Compound No. 81 )

(1) Flaked Mg (11.6 g, 0.477 mol) was placed in a 2 l capacity, three-neck flask, followed by adding THF (100 ml) in a nitrogen gas stream, dropwise adding a solution of 3,4,5-trifluorobromobenzene (91.6 g, 0.434 mol) in THF (200 ml) with stirring at a velocity of keeping 30° C., stirring the mixture at room temperature for 2 hours after completion of the dropwise addition, dropwise adding to the reaction solution, a solution of 4,4'-dicyclohexanedionemonoethylene acetal (94 g, 0.395 mol) in THF (200 ml) over 45 minutes so as to keep its temperature at 30° C. or lower, stirring the mixture at room temperature for 2 hours after completion of the dropwise addition, allowing the reaction solution to stand overnight, again stirring the reaction solution, adding a saturated aqueous solution of NH4Cl little by little, extracting the resulting solution three times with ethyl acetate (400 ml), washing the organic layer with water, drying it over anhydrous MgSO4, and concentrating under reduced pressure, to obtain 4-hydroxy-4-(3',4',5'-trifluorophenyl)dicyclohexaneethylene acetal (125 g, GC 79%) in the form of yellow-brown solids. This product was used for the subsequent reaction without purification.

(2) The above reaction product (125 g) was dissolved in toluene (500 ml), in a 2 l capacity three-neck flask equipped with Dean-Stark's device, followed by adding Amberlist-15 (6.5 g), heating the mixture under reflux with stirring for 4 hours, cooling the solution down to room temperature after completion of the reaction, filtering off the Amberlist-15, concentrating the mother liquor under reduced pressure and separating and purifying the residue according to silica gel chromatography, to obtain 4-(3', 4',5'-trifluorophenyl)-3'-dicyclohexen-4-one ethylene acetal (85 g). m.p. 107.0°–114.0° C.

(3) 4-(3',4',5'-Trifluorophenyl)-3'-dicyclohexen-4-one ethylene acetal (66 g) was placed in a 1 l capacity three-neck flask and dissolved in a mixed solvent of ethyl acetate/ethanol (3:1) (500 ml), followed by adding Pd/C (5 wt %) catalyst (5 g) to the solution, stirring the mixture in a hydrogen gas atmosphere, completing the stirring when absorption of the hydrogen gas was not observed, filtering off the catalyst and concentrating the resulting solution under reduced pressure, to obtain a transparent oily substance. This substance was recrystallized from ethanol and purified, to obtain trans-4-(3',4',5'-trifluorophenyl)dicyclohexane-4-one ethylene acetal (24 g). m.p. 101.0°–104.5° C.

(4) Trans-4-(3',4',5'-trifluorophenyl)-dicyclohexan-4one ethylene acetal (24 g) was placed in a 200 ml capacity, egg-plant type flask, followed by dissolving it in toluene (100 ml), adding formic acid (15.6 g) to the solution, heating the mixture under reflux with stirring for 4 hours, cooling it down to room temperature after completion of the reaction, adding ethyl acetate (200 ml), washing with water, drying the organic layer over anhydrous MgSO4, concentrating under reduced pressure to obtain white crystals, and recrystallizing them from n-heptane for purification, to obtain 4-(trans-4'-(3",4",5"-trifluorophenyl)cyclohexyl)cyclohexanone (17 g). m.p. 96.7°–99.6° C.

(5) Methoxymethyltriphenylphosphonium chloride (16.5 g) was placed in a 300 ml capacity three-neck flask, and added THF (100 ml) to obtain a suspension, followed by adding potassium-t-butoxide (6.5 g) to the suspension while keeping the temperature at −10° C. or lower, stirring the mixture at −10° C. for one hour, dropwise adding a solution of 4-(trans-4'-(3",4",5"-trifluorophenyl)cyclohexyl)-cyclohexanone (10 g) in THF (80 ml) at a speed of keeping −10° C., stirring the mixture at the temperature for one hour, further stirring at room temperature for 2 hours, adding water (100 ml) after completion of the reaction, extracting three times with ethyl acetate (100 ml), washing the organic layer with water, drying over anhydrous MgSO4, concentrating under reduced pressure to obtain white solids, and isolating and purifying them according to silica gel column chromatography, to obtain 4-(trans-4'-(3",4",5"-trifluorophenyl)cyclohexyl)methoxymethylenecyclohexane (10.2 g ) (white crystals). m.p. 78.4°–81.2° C.

(6) 4-(Trans-4'-(3",4",5"-trifluorophenyl)cyclohexyl)methoxymethylenecyclohexane (10.2 g) was placed in a 300 ml capacity egg-plant type flask, followed by adding THF (80 ml) to obtain a solution, adding 2N-hydrochloric acid (30 ml) to the solution, heating the mixture with stirring for 2 hours, cooling down to room temperature after completion of the reaction, adding water (30 ml), extracting three times with ethyl acetate (50 ml), washing the organic layer with water, drying over anhydrous MgSO$_4$, and concentrating under reduced pressure, to obtain 4-(trans-4'-(3",4",5"-trifluorophenyl)cyclohexyl)cyclohexanecarbaldehyde (6 g) (a transparent oily substance). This product was used for the subsequent reaction without purification.

(7) Methyltriphenylphosphonium bromide (14.0 g) was placed in a 300 ml capacity three-neck flask, followed by adding THF (100 ml) to obtain a suspension, adding potassium-t-butoxide (5.3 g) to the suspension while keeping a temperature of −10° C. or lower, stirring the mixture at −10° C. for one hour, dropwise adding a solution of 4-(trans-4'-(3",4",5"-trifluorophenyl)cyclohexyl)cyclohexanecarbaldehyde (8.5 g) in THF (100 ml) at a speed of keeping −10° C., stirring the mixture at the temperature for one hour, further stirring at room temperature for 2 hours, adding water (100 ml) after completion of the reaction, extracting three times with ethyl acetate (100 ml), washing the organic layer with water, drying over anhydrous MgSO$_4$ and concentrating under reduced pressure to obtain white solids. The aimed product was isolated from the solids according to silica gel column chromatography, recrystallized and purified to obtain trans-(4-(trans-4' -(3",4",5"-trifluorophenyl)cyclohexyl)cyclohexylethene (3.8 g) (white crystals). This product exhibited liquid crystal phases: C-N point, 57.1°–58.8° C. and N-I point, 69.2°–71.3° C.

The following compounds are prepared according to the above procedure:

82. 3-(4'-trans-(4"-trans-(3"',4"',5"'-trifluorophenyl)cyclohexyl)cyclohexyl)-2E-propene
83. 3-(4'-trans-(4"-trans-(3"',4"',5"'-trifluorophenyl)cyclohexyl)cyclohexyl)-1-propene
84. 4-(4'-trans-(4"-trans-(3"',4"',5"'-trifluorophenyl)cyclohexyl)cyclohexyl)-1-butene C-N point, 64.1° C. and N-I point, 99.1° C.
85. 4-(4'-trans-(4"-trans-(3"',4"',5"'-trifluorophenyl)cyclohexyl)cyclohexyl)-2E-butene
86. 4-(4'-trans-(4"-trans-(3"',4"',5"'-trifluorophenyl)cyclohexyl)cyclohexyl)-3E-butene
87. 5-(4'-trans-(4"-trans-(3"',4"',5"'-trifluorophenyl)cyclohexyl)cyclohexyl)-1-pentene
88. 5-(4'-trans-(4"-trans-(3"',4"',5"'-trifluorophenyl)cyclohexyl)cyclohexyl)-2E-pentene
89. 5-(4'-trans-(4"-trans-(3"',4"',5"'-trifluorophenyl)cyclohexyl)cyclohexyl)-3E-pentene
90. 5-(4'-trans-(4"-trans-(3"',4"',5"'-trifluorophenyl)cyclohexyl)cyclohexyl)-4E-pentene
91. 6-(4'-trans-(4"-trans-(3"',4"',5"'-trifluorophenyl)cyclohexyl)cyclohexyl)-1-hexene
92. 6-(4'-trans-(4"-trans-(3"',4"',5"'-trifluorophenyl)cyclohexyl)cyclohexyl)- 2E-hexene
93. 6-(4'-trans-(4"-trans-(3"',4"',5"'-trifluorophenyl)cyclohexyl)cyclohexyl)-3E-hexene
94. 6-(4'-trans-(4"-trans-(3"',4"',5"'-trifluorophenyl)cyclohexyl)cyclohexyl)-4E-hexene
95. 7-(4'-trans-(4"-trans-(3"',4"',5"'-trifluorophenyl)cyclohexyl)cyclohexyl)-2E-heptene
96. 7-(4'-trans-(4"-trans-(3"',4"',5"'-trifluorophenyl)cyclohexyl)cyclohexyl)-3E-heptene
97. 7-(4'-trans-(4"-trans-(3"',4"',5"'-trifluorophenyl)cyclohexyl)cyclohexyl)-4E-heptene
98. 8-(4'-trans-(4"-trans-(3"',4"',5"'-trifluorophenyl)cyclohexyl)cyclohexyl)-3E-octene
99. 8-(4'-trans-(4"-trans-(3"',4"',5"'-trifluorophenyl)cyclohexyl)cyclohexyl)-4E-octene
100. 9-(4'-trans-(4"-trans-(3"',4"',5"'-trifluorophenyl)cyclohexyl)cyclohexyl)-4E-nonene
101. 2-(4'-trans-(4"-trans-(3"',5"'-difluoro-4"'-trifluoromethylphenyl)cyclohexyl)ethene
102. 3-(4'-trans-(4"-trans-(3"',5"'-difluoro-4"'-trifluoromethylphenyl)cyclohexyl)cyclohexyl)-2E-propene
103. 3-(4'-trans-(4"-trans-(3"',5"'-difluoro-4"'-trifluoromethylphenyl)cyclohexyl)cyclohexyl)-1-propene
104. 4-(4'-trans-(4"-trans-(3"',5"'-difluoro-4"'-trifluoromethylphenyl)cyclohexyl)cyclohexyl)-1-butene
105. 4-(4'-trans-(4"-trans-(3"',5"'-difluoro-4"'-trifluoromethylphenyl)cyclohexyl)cyclohexyl)-2E-butene
106. 4-(4'-trans-(4"-trans-(3"',5"'-difluoro-4"'-trifluoromethylphenyl)cyclohexyl)cyclohexyl)-3E-butene
107. 5-(4'-trans-(4"-trans-(3"',5"'-difluoro-4"'-trifluoromethylphenyl)cyclohexyl)cyclohexyl)-1-pentene
108. 5-(4'-trans-(4"-trans-(3"',5"'-difluoro-4"'-trifluoromethylphenyl)cyclohexyl)cyclohexyl)-2E-pentene
109. 5-(4'-trans-(4"-trans-(3"',5"'-difluoro-4"'-trifluoromethylphenyl)cyclohexyl)cyclohexyl)-3E-pentene
110. 5-(4'-trans-(4"-trans-(3"',5"'-difluoro-4"'-trifluoromethylphenyl)cyclohexyl)cyclohexyl)-4E-pentene
111. 6-(4'-trans-(4"-trans-(3"',5"'-difluoro-4"'-trifluoromethylphenyl)cyclohexyl)cyclohexyl)-1-hexene
112. 6-(4'-trans-(4"-trans-(3"',5"'-difluoro-4"'-trifluoromethylphenyl)cyclohexyl)cyclohexyl)-2E-hexene
113. 6-(4'-trans-(4"-trans-(3"',5"'-difluoro-4"'-trifluoromethylphenyl)cyclohexyl)cyclohexyl)-3E-hexene
114. 6-(4'-trans-(4"-trans-(3"',5"'-difluoro-4"'-trifluoromethylphenyl)cyclohexyl)cyclohexyl)-4E-hexene
115. 7-(4'-trans-(4"-trans-(3"',5"'-difluoro-4"'-trifluoromethylphenyl)cyclohexyl)cyclohexyl)-2E-heptene
116. 7-(4'-trans-(4"-trans-(3"',5"'-difluoro-4"'-trifluoromethylphenyl)cyclohexyl)cyclohexyl)-3E-heptene 117. 7-(4'-trans-(4''-trans-(3''',5'''-difluoro-4''''-trifluoromethylphenyl)cyclohexyl)cyclohexyl)-4E-heptene
118. 8-(4'-trans-(4''-trans-(3''',5'''-difluoro-4''''-trifluoromethylphenyl)cyclohexyl)cyclohexyl)-3E-octene
119. 8-(4'-trans-(4''-trans-(3''',5'''-difluoro-4''''-trifluoromethylphenyl)cyclohexyl)cyclohexyl)-4E-octene
120. 9-(4'-trans-(4''-trans-(3''',5'''-difluoro-4''''-trifluoromethylphenyl)cyclohexyl)cyclohexyl)-4E-nonene
121. 2-(4'-trans-(4''-trans-(3''',5'''-difluoro-4''''-trifluoromethoxyphenyl)cyclohexyl)cyclohexyl)ethene
122. 3-(4'-trans-(4''-trans-(3''',5'''-difluoro-4''''-trifluoromethoxyphenyl)cyclohexyl)cyclohexyl)-2E-propene
123. 3-(4'-trans-(4''-trans-(3''',5'''-difluoro-4''''-trifluoromethoxyphenyl)cyclohexyl)cyclohexyl)-1-propene
124. 4-(4'-trans-(4''-trans-(3''',5'''-difluoro-4''''-trifluoromethoxyphenyl)cyclohexyl)cyclohexyl)-1-butene
125. 4-(4'-trans-(4''-trans-(3''',5'''-difluoro-4''''-trifluoromethoxyphenyl)cyclohexyl)cyclohexyl)-2E-butene
126. 4-(4'-trans-(4''-trans-(3''',5'''-difluoro-4''''-trifluoromethoxyphenyl)cyclohexyl)cyclohexyl)-3E-butene
127. 5-(4'-trans-(4''-trans-(3''',5'''-difluoro-4''''-trifluoromethoxyphenyl)cyclohexyl)cyclohexyl)-1-pentene
128. 5-(4'-trans-(4''-trans-(3''',5'''-difluoro-4''''-trifluoromethoxyphenyl)cyclohexyl)cyclohexyl)-2E-pentene
129. 5-(4'-trans-(4''-trans-(3''',5'''-difluoro-4''''-trifluoromethoxyphenyl)cyclohexyl)cyclohexyl)-3E-pentene
130. 5-(4'-trans-(4''-trans-(3''',5'''-difluoro-4''''-trifluoromethoxyphenyl)cyclohexyl)cyclohexyl-4E-pentene
131. 6-(4'-trans-(4''-trans-(3''',5'''-difluoro-4''''-trifluoromethoxyphenyl)cyclohexyl)cyclohexyl)-1-hexene
132. 6-(4'-trans-(4''-trans-(3''',5'''-difluoro-4''''-trifluoromethoxyphenyl)cyclohexyl)cyclohexyl)-2E-hexene
133. 6-(4'-trans-(4''-trans-(3''',5'''-difluoro-4''''-trifluoromethoxyphenyl)cyclohexyl)cyclohexyl)-3E-hexene
134. 6-(4'-trans-(4''-trans-(3''',5'''-difluoro-4''''-trifluoromethoxyphenyl)cyclohexyl)cyclohexyl)-4E-hexene
135. 7-(4'-trans-(4''-trans-(3''',5'''-difluoro-4''''-trifluoromethoxyphenyl)cyclohexyl)cyclohexyl)-2 E-heptene
136. 7-(4'-trans-(4''-trans-(3''',5'''-difluoro-4''''-trifluoromethoxyphenyl)cyclohexyl)cyclohexyl)-3E-heptene
137. 7-(4'-trans-(4''-trans-(3''',5'''-difluoro-4''''-trifluoromethoxyphenyl)cyclohexyl)cyclohexyl)-4E-heptene
138. 8-(4'-trans-(4''-trans-(3''',5'''-difluoro-4''''-trifluoromethoxyphenyl)cyclohexyl)cyclohexyl)-3E-octene
139. 8-(4'-trans-(4''-trans-(3''',5'''-difluoro-4''''-trifluoromethoxyphenyl)cyclohexyl)cyclohexyl)-4E-octene
140. 9-(4'-trans-(4''-trans-(3''',5'''-difluoro-4''''-trifluoromethoxyphenyl)cyclohexyl)cyclohexyl)-4E-nonene
141. 2-(4'-trans-(4''-trans-(3''',5'''-difluoro-4''''-difluoromethoxyphenyl)cyclohexyl)cyclohexyl)ethene
142. 3-(4'-trans-(4''-trans-(3''',5'''-difluoro-4''''-difluoromethoxyphenyl)cyclohexyl)cyclohexyl)-2E-propene
143. 3-(4'-trans-(4''-trans-(3''',5'''-difluoro-4''''-difluoromethoxyphenyl)cyclohexyl)cyclohexyl)-1-propene
144. 4-(4'-trans-(4''-trans-(3''',5'''-difluoro-4''''-difluoromethoxyphenyl)cyclohexyl)cyclohexyl)-1-butene
145. 4-(4'-trans-(4''-trans-(3''',5'''-difluoro-4''''-difluoromethoxyphenyl)cyclohexyl)cyclohexyl)-2E-butene
146. 4-(4'-trans-(4''-trans-(3''',5'''-difluoro-4''''-difluoromethoxyphenyl)cyclohexyl)cyclohexyl)-3E-butene
147. 5-(4'-trans-(4''-trans-(3''',5'''-difluoro-4''''-difluoromethoxyphenyl)cyclohexyl)cyclohexyl)-1-pentene
148. 5-(4'-trans-(4''-trans-(3''',5'''-difluoro-4''''-difluoromethoxyphenyl)cyclohexyl)cyclohexyl)-2E-pentene
149. 5-(4'-trans-(4''-trans-(3''',5'''-difluoro-4''''-difluoromethoxyphenyl)cyclohexyl)cyclohexyl)-3E-pentene
150. 5-(4'-trans-(4''-trans-(3''',5'''-difluoro-4''''-difluoromethoxyphenyl)cyclohexyl)cyclohexyl)-4E-pentene
151. 6-(4'-trans-(4''-trans-(3''',5'''-difluoro-4''''-difluoromethoxyphenyl)cyclohexyl)cyclohexyl)-1-hexene
152. 6-(4'-trans-(4''-trans-(3''',5'''-difluoro-4''''-difluoromethoxyphenyl)cyclohexyl)cyclohexyl)-2E-hexene
153. 6-(4'-trans-(4''-trans-(3''',5'''-difluoro-4''''-difluoromethoxyphenyl)cyclohexyl)cyclohexyl)-3E-hexene
154. 6-(4'-trans-(4''-trans-(3''',5'''-difluoro-4''''-difluoromethoxyphenyl)cyclohexyl)cyclohexyl)-4E-hexene
155. 7-(4'-trans-(4''-trans-(3''',5'''-difluoro-4''''-difluoromethoxyphenyl)cyclohexyl)cyclohexyl)-2E-heptene
156. 7-(4'-trans-(4''-trans-(3''',5'''-difluoro-4''''-difluoromethoxyphenyl)cyclohexyl)cyclohexyl)-3E-heptene
157. 7-(4'-trans-(4''-trans-(3''',5'''-difluoro-4''''-difluoromethoxyphenyl)cyclohexyl)cyclohexyl)-4E-heptene
158. 8-(4'-trans-(4''-trans-(3''',5'''-difluoro-4''''-difluoromethoxyphenyl)cyclohexyl)cyclohexyl)-3E-octene
159. 8-(4'-trans-(4''-trans-(3''',5'''-difluoro-4''''-difluoromethoxyphenyl)cyclohexyl)cyclohexyl)-4E-octene
160. 9-(4'-trans-(4''-trans-(3''',5'''-difluoro-4''''-difluoromethoxyphenyl)cyclohexyl)cyclohexyl)-4E-nonene Example 5

Preparation of 2-(4'-trans-(2''-(3''',4''',5'''-trifluorophenyl)ethyl)cyclohexyl)ethene (Compound No. 161)

(1) A suspension of 3,4,5-trifluorobenzyltriphenylphosphonium bromide (234 g) in THF (500 ml) was stirred in a nitrogen gas stream, followed by adding sodium methoxide (32.4 g) little by little at room temperature, stirring the reaction solution at room temperature for one hour, dropwise adding a solution of 4-formylcyclohexanone (50 g) in THF (250 ml), stirring the mixture at room temperature for 2 hours, adding it to water (1 l) extracting with ethyl acetate (1 l), washing the organic layer with water, drying over anhydrous MgSO4, concentrating the solvent under reduced pressure, to obtain 4-(2'-(3'',4'',5''-trifluorophenyl)ethenyl)cyclohexanone (71 g).

(2) 4-(2'-(3'',4'',5''-Trifluorophenyl)ethenyl)cyclohexanone (71 g) was dissolved in ethanol (500 ml), followed by adding Pd/C (5%) (2.0 g), hydrogenating the compound in a hydrogen gas atmosphere with stirring till the hydrogen absorption was completed, filtering off the catalyst after completion of the reaction, and concentrating the solvent under reduced pressure, to obtain 4-(2'-(3'',4'',5''-trifluorophenyl)ethyl)cyclohexanone (70 g).

(3) A suspension of methoxymethyltriphenylphosphonium chloride (112.3 g) in THF (300 ml) was stirred in a nitrogen gas stream, followed by adding potassium-t-butoxide (45.4 g) little by little while cooling at 0° C., stirring the reaction solution at room temperature for one hour, dropwise adding 4-(2'-(3'',4'',5''-trifluorophenyl)ethyl)cyclohexanone (70 g)in THF (200 ml), raising the temperature of the reaction mixture up to room temperature, further stirring for 2 hours, adding to water (500 ml) after completion of the reaction, extracting with ethyl acetate (500 ml), drying the organic layer over anhydrous MgSO4, concentrating under reduced pressure, and carrying out chromatography treatment on silica gel with ethyl acetate/heptane (1:5), to obtain 4-(2'-(3'',4'',5''-trifluorophenyl)ethyl)methoxymethylenecyclohexane (53.7 g).

(4) THF (100 ml) and 2N-hydrochloric acid (100 ml) were added to 4-(2'-(3'',4'',5''-trifluorophenyl)ethyl)methoxymethylenecyclohexane (20 g), followed by heating the mixture under reflux with stirring for 2 hours, adding to water (300 ml) after completion of the reaction, extracting with ethyl acetate (300 ml), drying the organic layer over anhydrous MgSO4 and concentrating under reduced pressure, to obtain 4-(2'-(3'',4'',5''-trifluorophenyl)ethyl)cyclohexane carbaldehyde (17 g).

(5) A suspension of methyltriphenylphosphonium bromide (27 W) in THF (50 ml) was stirred in a nitrogen gas stream, followed by adding potassium-t-butoxide little by little under cooling at 0° C., stirring the reaction solution at room temperature for one hour, dropwise adding a solution of 4-(2'-(3'',4'',5''-trifluorophenyl)ethyl)cyclohexanecarbaldehyde (17 g) in THF (50 ml), raising the temperature of the reaction mixture up to room temperature, further stirring it for 2 hours, adding to water (100 ml) after completion of the reaction, extracting with ethyl acetate (100 ml), drying the organic layer over anhydrous MgSO4, concentrating under reduced pressure, carrying out chromatography treatment on silica gel with ethyl acetate/heptane (1:5) and crystallizing from heptane, to obtain 2-(4'-trans-(2''-(3''',4''',5'''-trifluorophenyl)ethyl)cyclohexyl)ethene (9 g).

The following compounds are prepared according to the above procedure:

Compound Nos.

162. 3-(4'-trans-(2''-(3''',4''',5'''-trifluorophenyl)ethyl)cyclohexyl)-1-propene
163. 3-(4'-trans-(2''-(3''',4''',5'''-trifluorophenyl)ethyl)cyclohexyl)-2E-propene
164. 4-(4'-trans-(2''-(3''',4''',5'''-trifluorophenyl)ethyl)cyclohexyl)-1-butene
165. 4-(4'-trans-(2''-(3''',4''',5'''-trifluorophenyl)ethyl)cyclohexyl)-2E-butene
166. 4-(4'-trans-(2''-(3''',4''',5'''-trifluorophenyl)ethyl)cyclohexyl)-3E-butene
167. 5-(4'-trans-(2''-(3''',4''',5'''-trifluorophenyl)ethyl)cyclohexyl)-1-pentene
168. 5-(4'-trans-(2''-(3''',4''',5'''-trifluorophenyl)ethyl)cyclohexyl)-2E-pentene
169. 5-(4'-trans-(2''-(3''',4''',5'''-trifluorophenyl)ethyl)cyclohexyl)-3E-pentene
170. 5-(4'-trans-(2''-(3''',4''',5'''-trifluorophenyl)ethyl)cyclohexyl)-4E-pentene
171. 6-(4'-trans-(2''-(3''',4''',5'''-trifluorophenyl)ethyl)cyclohexyl)1-hexene
172. 6-(4'-trans-(2''-(3''',4''',5'''-trifluorophenyl)ethyl)cyclohexyl)-2E-hexene
173. 6-(4'-trans-(2''-(3''',4''',5'''-trifluorophenyl)ethyl)cyclohexyl)-3E-hexene
174. 6-(4'-trans-(2''-(3''',4''',5'''-trifluorophenyl)ethyl)cyclohexyl)-4E-hexene
175. 7-(4'-trans-(2''-(3''',4''',5'''-trifluorophenyl)ethyl)cyclohexyl)-2E-heptene
176. 7-(4'-trans-(2''-(3''',4''',5'''-trifluorophenyl)ethyl)cyclohexyl)-3E-heptene
177. 7-(4'-trans-(2''-(3''',4''',5'''-trifluorophenyl)ethyl)cyclohexyl)-4E-heptene
178. 8-(4'-trans-(2''-(3''',4''',5'''-trifluorophenyl)ethyl)cyclohexyl)-3E-octene
179. 8-(4'-trans-(2''-(3''',4''',5'''-trifluorophenyl)ethyl)cyclohexyl)-4E-octene
180. 9-(4'-trans-(2''-(3''',4''',5'''-trifluorophenyl)ethyl)cyclohexyl)-4E-nonene
181. 2-(4'-trans-(2''-(3''',5'''-difluoro-4'''-trifluoromethylphenyl)ethyl)cyclohexyl)ethene
182. 3-(4'-trans-(2''-(3''',5'''-difluoro-4'''-trifluoromethylphenyl)ethyl)cyclohexyl)-2E-propene
183. 3-(4'-trans-(2''-(3''',5'''-difluoro-4'''-trifluoromethylphenyl)ethyl)cyclohexyl)-1-propene
184. 4-(4'-trans-(2''-(3''',5'''-difluoro-4'''-trifluoromethylphenyl)ethyl)cyclohexyl)-1-butene
185. 4-(4'-trans-(2''-(3''',5'''-difluoro-4'''-trifluoromethylphenyl)ethyl)cyclohexyl)-2E-butene
186. 4-(4'-trans-(2''-(3''',5'''-difluoro-4'''-trifluoromethylphenyl)ethyl)cyclohexyl)-3E-butene
187. 5-(4'-trans-(2''-(3''',5'''-difluoro-4'''-trifluoromethylphenyl)ethyl)cyclohexyl)-1-pentene
188. 5-(4'-trans-(2''-(3''',5'''-difluoro-4'''-trifluoromethylphenyl)ethyl)cyclohexyl)-2E-pentene
189. 5-(4'-trans-(2''-(3''',5'''-difluoro-4'''-trifluoromethylphenyl)ethyl)cyclohexyl)-3E-pentene
190. 5-(4'-trans-(2''-(3''',5'''-difluoro-4'''-trifluoromethylphenyl)ethyl)cyclohexyl)-4E-pentene
191. 6-(4'-trans-(2''-(3''',5'''-difluoro-4'''-trifluoromethylphenyl)ethyl)cyclohexyl) -1-hexene
192. 6-(4'-trans-(2''-(3''',5'''-difluoro-4'''-trifluoromethylphenyl)ethyl)cyclohexyl)-2E-hexene 193. 6-(4'-trans-(2''-(3''',5'''-difluoro-4'''-trifluoromethylphenyl)ethyl)cyclohexyl)-3E-hexene
194. 6-(4'-trans-(2''-(3''',5'''-difluoro-4'''-trifluoromethylphenyl)ethyl)cyclohexyl)-4E-hexene
195. 7-(4'-trans-(2''-(3''',5'''-difluoro-4'''-trifluoromethylphenyl)ethyl)cyclohexyl)-2E-heptene
196. 7-(4'-trans-(2''-(3''',5'''-difluoro-4'''-trifluoromethylphenyl)ethyl)cyclohexyl)-3E-heptene
197. 7-(4'-trans-(2'-(3''',5'''-difluoro-4'''-trifluoromethylphenyl)ethyl)cyclohexyl)-4E-heptene
198. 8-(4'-trans-(2''-(3''',5'''-difluoro-4'''-trifluoromethylphenyl)ethyl)cyclohexyl)-3E-octene
199. 8-(4'-trans-(2''-(3''',5'''-difluoro-4'''-trifluoromethylphenyl)ethyl)cyclohexyl)-4E-octene
200. 8-(4'-trans-(2''-(3''',5'''-difluoro-4'''-trifluoromethylphenyl)ethyl)cyclohexyl)-4E-nonene
201. 2-(4'-trans-(2''-(3''',5'''-difluoro-4'''-trifluoromethoxylphenyl)ethyl)cyclohexyl)ethene
202. 3-(4'-trans-(2''-(3''',5'''-difluoro-4'''-trifluoromethoxylphenyl)ethyl)cyclohexyl)-2E-propene
203. 3-(4'-trans-(2''-(3''',5'''-difluoro-4'''-trifluoromethoxylphenyl)-ethyl)cyclohexyl)-1-propene
204. 4-(4'-trans-(2''-(3''',5'''-difluoro-4'''-trifluoromethoxylphenyl)ethyl)cyclohexyl)-1-butene
205. 4-(4'-trans-(2''-(3''',5'''-difluoro-4'''-trifluoromethoxylphenyl)ethyl)cyclohexyl)-2E-butene
206. 4-(4'-trans-(2''-(3''',5'''-difluoro-4'''-trifluoromethoxylphenyl)ethyl)cyclohexyl)-3E-butene
207. 5-(4'-trans-(2''-(3''',5'''-difluoro-4'''-trifluoromethoxylphenyl)ethyl)cyclohexyl)-1-pentene
208. 5-(4'-trans-(2''-(3''',5'''-difluoro-4'''-trifluoromethoxylphenyl)ethyl)cyclohexyl)-2E-pentene
209. 5-(4'-trans-(2''-(3''', 5'''-difluoro-4'''-trifluoromethoxylphenyl)ethyl)cyclohexyl)-3E-pentene
210. 5-(4'-trans-(2''-(3''',5'''-difluoro-4'''-trifluoromethoxylphenyl)ethyl)cyclohexyl)-4E-pentene
211. 6-(4'-trans-(2''-(3''',5'''-difluoro-4'''-trifluoromethoxylphenyl)ethyl)cyclohexyl)-1-hexene
212. 6-(4'-trans-(2''-(3''',5'''-difluoro-4'''-trifluoromethoxylphenyl)ethyl)cyclohexyl)-2E-hexene
213. 6-(4'-trans-(2''-(3''',5'''-difluoro-4'''-trifluoromethoxylphenyl)ethyl)cyclohexyl)-3E-hexene
214. 6-(4'-trans-(2''-(3''',5'''-difluoro-4'''-trifluoromethoxylphenyl)ethyl)cyclohexyl -4 E-hexene
215. 7-(4'-trans-(2''-(3''',5'''-difluoro-4'''-trifluoromethoxylphenyl)ethyl)cyclohexyl)-2E-heptene
216. 7-(4'-trans-(2''-(3''',5'''-difluoro-4'''-trifluoromethoxylphenyl)ethyl)cyclohexyl)-3E-heptene
217. 7-(4'-trans-(2''-(3''',5'''-difluoro-4'''-trifluoromethoxylphenyl)ethyl)cyclohexyl)-4E-heptene
218. 8-(4'-trans-(2''-(3''',5'''-difluoro-4'''-trifluoromethoxylphenyl)ethyl)cyclohexyl)-3E-octene
219. 8-(4'-trans-(2''-(3''',5'''-difluoro-4'''-trifluoromethoxylphenyl)ethyl)cyclohexyl)-4E-octene
220. 9-(4'-trans-(2''-(3''',5'''-difluoro-4'''-trifluoromethoxylphenyl)ethyl)cyclohexyl)-4E-nonene
221. 2-(4'-trans-(2''-(3''',5'''-difluoro-4'''-difluoromethoxylphenyl)ethyl)cyclohexyl)ethene
222. 3-(4'-trans-(2''-(3''',5'''-difluoro-4'''-difluoromethoxylphenyl)ethyl)cyclohexyl)-2E-propene
223. 3-(4'-trans-(2''-(3''',5'''-difluoro-4'''-difluoromethoxylphenyl)ethyl)cyclohexyl)-1-propene
224. 4-(4'-trans-(2''-(3''',5'''-difluoro-4'''-difluoromethoxylphenyl)ethyl)cyclohexyl)-1-butene
225. 4-(4'-trans-(2''-(3''',5'''-difluoro-4'''-difluoromethoxylphenyl)ethyl)cyclohexyl)-2E-butene
226. 4-(4'-trans-(2''-(3''',5'''-difluoro-4'''-difluoromethoxylphenyl)ethyl)cyclohexyl)-3E-butene
227. 5-(4'-trans-(2''-(3''',5'''-difluoro-4'''-difluoromethoxylphenyl)ethyl)cyclohexyl)-1-pentene
228. 5-(4'-trans-(2''-(3''',5'''-difluoro-4'''-difluoromethoxylphenyl)ethyl)cyclohexyl)-2E-pentene
229. 5-(4'-trans-(2''-(3''',5'''-difluoro-4'''-difluoromethoxylphenyl)ethyl)cyclohexyl)-3E-pentene
230. 5-(4'-trans-(2''-(3''',5'''-difluoro-4'''-difluoromethoxylphenyl)ethyl)cyclohexyl)-4E-pentene
231. 6-(4'-trans-(2''-(3''',5'''-difluoro-4'''-difluoromethoxylphenyl)ethyl)cyclohexyl)-1-hexene
232. 6-(4'-trans-(2''-(3''',5'''-difluoro-4'''-difluoromethoxylphenyl)ethyl)cyclohexyl)-2E-hexene
233. 6-(4'-trans-(2''-(3''',5'''-difluoro-4'''-difluoromethoxylphenyl)ethyl)cyclohexyl)-3E-hexene
234. 6-(4'-trans-(2''-(3''',5'''-difluoro-4'''-difluoromethoxylphenyl)ethyl)cyclohexyl)-4E-hexene
235. 7-(4'-trans-(2''-(3''',5'''-difluoro-4'''-difluoromethoxylphenyl)ethyl)cyclohexyl)-2E-heptene
236. 7-(4'-trans-(2''-(3''',5'''-difluoro-4'''-difluoromethoxylphenyl)ethyl)cyclohexyl)-3E-heptene
237. 7-(4'-trans-(2''-(3''',5'''-difluoro-4'''-difluoromethoxylphenyl)ethyl)cyclohexyl)-4E-heptene
238. 8-(4'-trans-(2''-(3''',5'''-difluoro-4'''-difluoromethoxylphenyl)ethyl)cyclohexyl)-3E-octene
239. 8-(4'-trans-(2''-(3''',5'''-difluoro-4'''-difluoromethoxylphenyl)ethyl)cyclohexyl)-4E-octene
240. 9-(4'-trans-(2''-(3''',5'''-difluoro-4'''-difluoromethoxylphenyl)ethyl)cyclohexyl)-4E-nonene Example 6

Preparation of 2-(4'-trans-(2''-(4'''-trans-(3'''',4'''',5''''-trifluorophenyl)cyclohexyl)ethyl)cyclohexyl)ethene (Compound No. 241)

(1) A suspension of triethyl phosphonoacetate (21.8 g) in THF (50 ml) was stirred in a nitrogen gas stream, followed by adding potassium-t-butoxide (11.8 g) little by little at room temperature, stirring the reaction solution at room temperature for one hour, dropwise adding a solution of 4-(3',4',5'-trifluorophenyl)cyclohexanone (20 g) in THF (50 ml), stirring at room temperature for 2 hours, adding to water (100 ml), extracting with ethyl acetate (100 ml), washing the organic layer with water, drying over anhydrous MgSO$_4$ and concentrating the solvent under reduced pressure, to obtain 4-(3',4',5'-trifluorophenyl))ethoxycarbonylmethylenecyclohexane (18.3 g).

(2) 4-(3',4',5'-Trifluorophenyl)ethoxycarbonylmethylenecyclohexane (18.3 g) was dissolved in ethanol (100 ml), followed by adding Pd/C (5%, 5 g), stirring the mixture, hydrogenating in a hydrogen gas atmosphere until completion of absorption of a hydrogen, filtering off the catalyst after completion of the reaction, and concentrating the solvent under reduced pressure, to obtain 4-(3',4',5'-trifluorophenyl)ethoxycarbonylmethylcyclohexane (17.2 g).

(3) Lithiumaluminium hydride (2.2 g) was added to a solution of 4-(3',4',5'-trifluorophenyl)ethoxycarbonylmethylcyclohexane (17.2 g) in THF (100 ml), followed by stirring the mixture at room temperature for 2 hours, adding ethyl acetate (100 ml) little by little after completion of the reaction, further adding 2N hydrochloric acid (50 ml), washing the organic layer with water, drying over anhydrous MgSO$_4$ and concentrating the solvent under reduced pressure, to obtain 4-(3',4',5'-trifluorophenyl)-1-(2'hydroxyethyl)cyclohexane (10.4 g).

(4) 4-(3',4',5'-Trifluorophenyl)-1-(2'-hydroxyethyl)-cyclohexane (10.4 g) was added to an aqueous solution of 47% HBr (15 ml), followed by stirring the mixture under reflux for 2 hours, adding the reaction solution to water (50 ml), extracting with ethyl acetate (100 ml), washing the organic layer with water, drying over anhydrous MgSO$_4$, and concentrating the solvent under reduced pressure, to obtain 4-(3',4',5'-trifluorophenyl)-1-(2'-bromoethyl)cyclohexane (10.4g).

(5) Mg (0.7 g) was suspended in THF (10 ml) in a nitrogen gas stream, followed by dropwise adding a solution of 4-(3',4',5'-trifluorophenyl)-1-(2'-bromoethyl)cyclohexane (9.8 g) in THF (50 ml), into the suspension, stirring the mixture at room temperature for one hour, dropwise adding a solution of 1,4-cyclohexanedionemonoethylene ketal (4 g) in THF (30 ml), stirring the mixture at room temperature for one hour, adding a saturated aqueous solution of NH$_4$Cl (100 ml) after completion of the reaction, extracting with ethyl acetate (100 ml), drying the organic layer over anhydrous MgSO$_4$ and distilling off the solvent under reduced pressure, to obtain 1,1-ethylenedioxy-4-hydroxy-4-(2'-(4''-(3''',4''', 5'''-trifluorophenyl)cyclohexyl)ethyl-cyclohexane 8.2 g).

(6) p-Toluenesulfonic acidmonohydrate (1 g) was added to a solution of 1,1-ethylenedioxy-4-hydroxy-4-(2'-(4''-(3''',4''', 5'''-trifluorophenyl)cyclohexyl)ethylcyclohexane (8.2 g) in toluene (100 ml), followed by stirring the mixture under reflux for one hour, washing the reaction solution with water (100 ml), drying the organic layer over anhydrous MgSO$_4$, and distilling off the solvent under reduced pressure, to obtain 1,1-ethylenedioxy-(2'-(4''-(3''',4''',5'''-trifluorophenyl)cyclohexyl)ethyl)-3-cyclohexene (6.7 g).

(7) Pd/C (5%) (1 g) was added to a solution of 1,1-ethylenedioxy-(2'-(4''-(3''',4''',5'''-trifluorophenyl)-cyclohexyl)-ethyl)-3-cyclohexene (6.7 g) in ethanol (200 ml), followed by carrying out catalytic reduction in a hydrogen gas atmosphere, filtering off the catalyst after completion of the reaction and distilling off the solvent from the organic layer under reduced pressure, to obtain 1,1-ethylenedioxy-(2'-(4''-(3''',4''',5'''-trifluorophenyl)cyclohexyl)ethyl)-cyclohexane (6.2 g).

(8) Formic acid (5 g, and toluene (2 ml) were added to 1,1-ethylenedioxy-(2'-(4''-(3''',4''',5'''-trifluorophenyl)cyclohexyl)ethyl)cyclohexane (6.2 g), followed by heating the mixture under reflux with stirring for 2 hours, pouring the reaction solution into water (20 ml), extracting with ethyl acetate (50 ml), drying the organic layer over anhydrous MgSO$_4$, distilling off the solvent under reduced pressure, and recrystallizing from ethanol, to obtain 4-(2'-(4''-trans (3''',4''',5'''-trifluorophenyl)cyclohexyl)ethyl)cyclohexanone (4.9 g).

(9) A suspension of methoxymethyltriphenylphosphonium chloride (6.2 g) in THF (50 ml) was stirred in a nitrogen gas stream, followed by adding potassium-t-butoxide (2 g) little by little while cooling at 0° C., stirring the reaction solution at room temperature for one hour, dropwise adding a solution of 4-(2'-(4''-trans-(3''',4''',5'''-trifluorophenyl)-cyclohexyl)ethyl)cyclohexanone (4.9 g) in THF (20 ml), raising the temperature of the reaction mixture up to room temperature, further stirring for 2 hours, adding to water (100 ml) after completion of the reaction, extracting with ethyl acetate (100 ml), drying the organic layer over anhydrous MgSO$_4$, concentrating under reduced pressure, and carrying out chromatography treatment in silica gel with ethyl acetate/heptane (1:5), to obtain 4-(2'-(4''-trans-(3''',4''',5'''-trifluorophenyl)cyclohexyl)ethyl)methoxymethylenecyclohexane 3.8 g).

(10) THF (10 ml) and 2N hydrochloric acid (10 ml) were added to 4-(2'-(4''-trans-(3''',4''',5'''-trifluorophenyl)cyclohexyl)ethyl)methoxymethylenecyclohexane (3.8 g), followed by heating the mixture under reflux with stirring for 2 hours, adding to water (50 ml) after completion of the reaction, extracting with ethyl acetate (50 ml), drying the organic layer over anhydrous MgSO$_4$ and concentrating under reduced pressure, to obtain 4-(2'-(4''-trans-(3''',4''',5'''-trifluorophenyl)cyclohexyl)ethyl)cyclohexanecarbaldehyde (3.5 g).

(11) A suspension of methyltriphenylphosphonium bromide (3.5 g) in THF (20 ml) was stirred in a nitrogen gas stream, followed by cooling it down to 0° C., adding potassium-t-butoxide (13 g) little by little, stirring the reaction solution at room temperature for one hour, dropwise adding a solution of 4-(2'-(4''-trans-(3''',4''',5'''-trifluorophenyl)cyclohexyl)ethyl)cyclohexanecarbaldehyde (3.5 g) in THF (20 ml), raising the temperature of the reaction mixture up to room temperature, further stirring for 2 hours, adding to water (50 ml) after completion of the reaction, extracting with ethyl acetate (100 ml), drying the organic layer over anhydrous MgSO$_4$, concentrating under reduced pressure, carrying out chromatography treatment on silica gel with ethyl acetate/heptane (1:5) and recrystallizing from heptane, to obtain 2-(4'-trans-(2''-(4'''-trans-(3'''',4'''',5''''-trifluorophenyl)cyclohexyl)ethyl)cyclohexyl)ethene (2.2g).

The following compounds are prepared according to the above procedure:

Compound Nos.

242. 3-(4'-trans-(2''-(4'''-trans-(3'''',4'''',5''''-trifluorophenyl)cyclohexyl)ethyl)cyclohexyl)-1-propene
243. 3-(4'-trans-(2''-(4'''-trans-(3'''',4'''',5''''-trifluorophenyl)cyclohexyl)ethyl)cyclohexyl)-2E-propene
244. 4-(4'-trans-(2''-(4'''-trans-(3'''', 4'''',5''''-trifluorophenyl)cyclohexyl)ethyl)cyclohexyl)-1-butene
245. 4-(4'-trans-(2''-(4'''-trans-(3'''',4'''',5''''-trifluorophenyl)cyclohexyl)ethyl)cyclohexyl)-2E-butene
246. 4-(4'-trans-(2''-(4'''-trans-(3'''',4'''',5''''-trifluorophenyl)cyclohexyl)ethyl)cyclohexyl)-3E-butene
247. 5-(4'-trans-(2''-(4'''-trans-(3'''',4'''',5''''-trifluorophenyl)cyclohexyl)ethyl)cyclohexyl)-1-pentene
248. 5-(4'-trans-(2''-(4'''-trans-(3'''',4'''',5''''-trifluorophenyl)cyclohexyl)ethyl)cyclohexyl)-2E-pentene
249. 5-(4'-trans-(2''-(4'''-trans-(3'''',4'''',5''''-trifluorophenyl)cyclohexyl)ethyl)cyclohexyl)-3E-pentene
250. 5-(4'-trans-(2''-(4'''-trans-(3'''',4'''',5''''-trifluorophenyl)cyclohexyl)ethyl)cyclohexyl)-4E-pentene
251. 6-(4'-trans-(2''-(4'''-trans-(3'''',4'''',5''''-trifluorophenyl)cyclohexyl)ethyl)cyclohexyl)-1-hexene
252. 6-(4'-trans-(2''-(4'''-trans-(3'''',4'''',5''''-trifluorophenyl)cyclohexyl)ethyl)cyclohexyl)-2E-hexene
253. 6-(4'-trans-(2''-(4'''-trans-(3'''',4'''',5''''-trifluorophenyl)cyclohexyl)ethyl)cyclohexyl)-3E-hexene 254. 6-(4'-trans-(2''-(4'''-trans-(3'''',4'''',5''''-trifluorophenyl)cyclohexyl)ethyl)cyclohexyl)-4E-hexene
255. 7-(4'-trans-(2''-(4'''-trans-(3'''',4'''',5''''-trifluorophenyl)cyclohexyl)ethyl)cyclohexyl)-2E-heptene
256. 7-(4'-trans-(2''-(4'''-trans-(3'''',4'''',5''''-trifluorophenyl)cyclohexyl)ethyl)cyclohexyl)-3E-heptene
257. 7-(4'-trans-(2''-(4'''-trans-(3'''',4'''',5''''-trifluorophenyl)cyclohexyl)ethyl)cyclohexyl)-4E-heptene
258. 8-(4'-trans-(2''-(4'''-trans-(3'''',4'''',5''''-trifluorophenyl)cyclohexyl)ethyl)cyclohexyl)-3E-octene
259. 8-(4'-trans-(2''-(4'''-trans-(3'''',4'''',5''''-trifluorophenyl)cyclohexyl)ethyl)cyclohexyl)-4E-octene
260. 9-(4'-trans-(2''-(4'''-trans-(3'''',4'''',5''''-trifluorophenyl)cyclohexyl)ethyl)cyclohexyl)-4E-nonene
261. 2-(4'-trans-(2''-(4'''-trans-(3'''',5''''-difluoro-4''''-trifluoromethylphenyl)cyclohexyl)ethyl)cyclohexyl)ethene
262. 3-(4'-trans-(2''-(4'''-trans-(3'''',5''''-difluoro-4''''-trifluoromethylphenyl)cyclohexyl)ethyl)cyclohexyl)-2E-propene
263. 3-(4'-trans-(2''-(4'''-trans-(3'''',5''''-difluoro-4''''-trifluoromethylphenyl)cyclohexyl)ethyl)cyclohexyl)-1-propene
264. 4-(4'-trans-(2''-(4'''-trans-(3'''',5''''-difluoro-4''''-trifluoromethylphenyl)cyclohexyl)ethyl)cyclohexyl)-1-butene
265. 4-(4'-trans-(2''-(4'''-trans-(3'''',5''''-difluoro-4''''-trifluoromethylphenyl)cyclohexyl)ethyl)cyclohexyl)-2E-butene
266. 4-(4'-trans-(2''-(4'''-trans-(3'''',5''''-difluoro-4''''-trifluoromethylphenyl)cyclohexyl)ethyl)cyclohexyl)-3E-butene
267. 5-(4'-trans-(2''-(4'''-trans-(3'''',5''''-difluoro-4''''-trifluoromethylphenyl)cyclohexyl)ethyl)cyclohexyl)-1-pentene
268. 5-(4'-trans-(2''-(4'''-trans-(3'''',5''''-difluoro-4''''-trifluoromethylphenyl)cyclohexyl)ethyl)cyclohexyl)-2E-pentene
269. 5-(4'-trans-(2''-(4'''-trans-(3'''',5''''-difluoro-4''''-trifluoromethylphenyl)cyclohexyl)ethyl)cyclohexyl)-3E-pentene
270. 5-(4'-trans-(2''-(4'''-trans-(3'''',5''''-difluoro-4''''-trifluoromethylphenyl)cyclohexyl)ethyl)cyclohexyl)-4E-pentene
271. 6-(4'-trans-(2''-(4'''-trans-(3'''',5''''-difluoro-4''''-trifluoromethylphenyl)cyclohexyl)ethyl)cyclohexyl)-1-hexene
272. 6-(4'-trans-(2''-(4'''-trans-(3'''',5''''-difluoro-4''''-trifluoromethylphenyl)cyclohexyl)ethyl)cyclohexyl)-2E-hexene
273. 6-(4'-trans-(2''-(4'''-trans-(3'''',5''''-difluoro-4''''-trifluoromethylphenyl)cyclohexyl)ethyl)cyclohexyl)-3E-hexene
274. 6-(4'-trans-(2''-(4'''-trans-(3'''',5''''-difluoro-4''''-trifluoromethylphenyl)cyclohexyl)ethyl)cyclohexyl)-4E-hexene
275. 7-(4'-trans-(2''-(4'''-trans-(3'''',5''''-difluoro-4''''-trifluoromethylphenyl)cyclohexyl)ethyl)cyclohexyl)-2E-heptene
276. 7-(4'-trans-(2''-(4'''-trans-(3'''',5''''-difluoro-4''''-trifluoromethylphenyl)cyclohexyl)ethyl)cyclohexyl)-3E-heptene
277. 7-(4'-trans-(2''-(4'''-trans-(3'''',5''''-difluoro-4''''-trifluoromethylphenyl)cyclohexyl)ethyl)cyclohexyl)-4E-heptene
278. 8-(4'-trans-(2''-(4'''-trans-(3'''',5''''-difluoro-4''''-trifluoromethylphenyl)cyclohexyl)ethyl)cyclohexyl)-3E-octene
279. 8-(4'-trans-(2''-(4'''-trans-(3'''',5''''-difluoro-4''''-trifluoromethylphenyl)cyclohexyl)ethyl)cyclohexyl)-4E-octene
280. 9-(4'-trans-(2''-(4'''-trans-(3'''',5''''-difluoro-4''''-trifluoromethylphenyl)cyclohexyl)ethyl)cyclohexyl)-4E-nonene
281. 2-(4'-trans-(2''-(4'''-trans-(3'''',5''''-difluoro-4''''-trifluoromethoxyphenyl)cyclohexyl)ethyl)cyclohexyl)ethene
282. 3-(4'-trans-(2''-(4'''-trans-(3'''',5''''-difluoro-4''''-trifluoromethoxyphenyl)cyclohexyl)ethyl)cyclohexyl)-2E-propene
283. 3-(4'-trans-(2''-(4'''-trans-(3'''',5''''-difluoro-4''''-trifluoromethoxyphenyl)cyclohexyl)ethyl)cyclohexyl)-1-propene
284. 4-(4'-trans-(2''-(4'''-trans-(3'''',5''''-difluoro-4''''-trifluoromethoxyphenyl)cyclohexyl)ethyl)cyclohexyl)-1-butene
285. 4-(4'-trans-(2''-(4'''-trans-(3'''',5''''-difluoro-4''''-trifluoromethoxyphenyl)cyclohexyl)ethyl)cyclohexyl)-2E-butene
286. 4-(4'-trans-(2''-(4'''-trans-(3'''',5''''-difluoro-4''''-trifluoromethoxyphenyl)cyclohexyl)ethyl)cyclohexyl)-3E-butene
287. 5-(4'-trans-(2''-(4'''-trans-(3'''',5''''-difluoro-4''''-trifluoromethoxyphenyl)cyclohexyl)ethyl)cyclohexyl)1-pentene
288. 5-(4'-trans-(2''-(4'''-trans-(3'''',5''''-difluoro-4''''-trifluoromethoxyphenyl)cyclohexyl)ethyl)cyclohexyl)-2E-pentene
289. 5-(4'-trans-(2''-(4'''-trans-(3'''',5''''-difluoro-4''''-trifluoromethoxyphenyl)cyclohexyl)ethyl)cyclohexyl)-3E-pentene
290. 5-(4'-trans-(2''-(4'''-trans-(3'''',5''''-difluoro-4''''-trifluoromethoxyphenyl)cyclohexyl)ethyl)cyclohexyl)-4E-pentene
291. 6-(4'-trans-(2''-(4'''-trans-(3'''',5''''-difluoro-4''''-trifluoromethoxyphenyl)cyclohexyl)ethyl)cyclohexyl)-1-hexene
292. 6-(4'-trans-(2''-(4'''-trans-(3'''',5''''-difluoro-4''''-trifluoromethoxyphenyl)cyclohexyl)ethyl)cyclohexyl)-2E-hexene
293. 6-(4'-trans-(2''-(4'''-trans-(3'''',5''''-difluoro-4''''-trifluoromethoxyphenyl)cyclohexyl)ethyl)cyclohexyl)-3E-hexene
294. 6-(4'-trans-(2''-(4'''-trans-(3'''',5''''-difluoro-4''''-trifluoromethoxyphenyl)cyclohexyl)ethyl)cyclohexyl)-4E-hexene
295. 7-(4'-trans-(2''-(4'''-trans-(3'''',5''''-difluoro-4''''-trifluoromethoxyphenyl)cyclohexyl)ethyl)cyclohexyl)-2E-heptene
296. 7-(4'-trans-(2''-(4'''-trans-(3'''',5''''-difluoro-4''''-trifluoromethoxyphenyl)cyclohexyl)ethyl)cyclohexyl)-3E-heptene
297. 7-(4'-trans-(2''-(4'''-trans-(3'''',5''''-difluoro-4''''-trifluoromethoxyphenyl)cyclohexyl)ethyl)cyclohexyl)-4E-heptene
298. 8-(4'-trans-(2''-(4'''-trans-(3'''',5''''-difluoro-4''''-trifluoromethoxyphenyl)cyclohexyl)ethyl)cyclohexyl)-3E-octene
299. 8-(4'-trans-(2''-(4'''-trans-(3'''',5''''-difluoro-4''''-trifluoromethoxyphenyl)cyclohexyl)ethyl)cyclohexyl)-4E-octene
300. 9-(4'-trans-(2''-(4'''-trans-(3'''',5''''-difluoro-4''''-trifluoromethoxyphenyl)cyclohexyl)ethyl)cyclohexyl)-4E-nonene 301. 2-(4'-trans-(2''-(4'''-trans-(3'''',5''''-difluoro-4''''-difluoromethoxyphenyl)cyclohexyl)ethyl)cyclohexyl)ethene
302. 3-(4'-trans-(2''-(4'''-trans-(3'''',5''''-difluoro-4''''-difluoromethoxyphenyl)cyclohexyl)ethyl)cyclohexyl)-2E-propene
303. 3-(4'-trans-(2''-(4'''-trans-(3'''',5''''-difluoro-4''''-difluoromethoxyphenyl)cyclohexyl)ethyl)cyclohexyl)1-propene
304. 4-(4'-trans-(2''-(4'''-trans-(3'''',5''''-difluoro-4''''-difluoromethoxyphenyl)cyclohexyl)ethyl)cyclohexyl)-1-butene
305. 4-(4'-trans-(2''-(4'''-trans-(3'''',5''''-difluoro-4''''-difluoromethoxyphenyl)cyclohexyl)ethyl)cyclohexyl)-2E-butene
306. 4-(4'-trans-(2''-(4'''-trans-(3'''',5''''-difluoro-4''''-difluoromethoxyphenyl)cyclohexyl)ethyl)cyclohexyl)-3E-butene
307. 5-(4'-trans-(2''-(4'''-trans-(3'''',5''''-difluoro-4''''-difluoromethoxyphenyl)cyclohexyl)ethyl)cyclohexyl)-1-pentene
308. 5-(4'-trans-(2''-(4'''-trans-(3'''',5''''-difluoro-4''''-difluoromethoxyphenyl)cyclohexyl)ethyl)cyclohexyl)-2E-pentene
309. 5-(4'-trans-(2''-(4'''-trans-(3'''',5''''-difluoro-4''''-difluoromethoxyphenyl)cyclohexyl)ethyl)cyclohexyl)-3E-pentene
310. 5-(4'-trans-(2''-(4'''-trans-(3'''',5''''-difluoro-4''''-difluoromethoxyphenyl)cyclohexyl)ethyl)cyclohexyl)-4E-pentene
311. 6-(4'-trans-(2''-(4'''-trans-(3'''',5''''-difluoro-4''''-difluoromethoxyphenyl)cyclohexyl)ethyl)cyclohexyl)-1-hexene
312. 6-(4'-trans-(2''-(4'''-trans-(3'''',5''''-difluoro-4''''-difluoromethoxyphenyl)cyclohexyl)ethyl)cyclohexyl)-2E-hexene
313. 6-(4'-trans-(2''-(4'''-trans-(3'''',5''''-difluoro-4''''-difluoromethoxyphenyl)cyclohexyl)ethyl)cyclohexyl)-3E-hexene
314. 6-(4'-trans-(2''-(4'''-trans-(3'''',5''''-difluoro-4''''-difluoromethoxyphenyl)cyclohexyl)ethyl)cyclohexyl)-4E-hexene
315. 7-(4'-trans-(2''-(4'''-trans-(3'''',5''''-difluoro-4''''-difluoromethoxyphenyl)cyclohexyl)ethyl)cyclohexyl)-2E-heptene
316. 7-(4'-trans-(2''-(4'''-trans-(3'''',5''''-difluoro-4''''-difluoromethoxyphenyl)cyclohexyl)ethyl)cyclohexyl)-3E-heptene
317. 7-(4'-trans-(2''-(4'''-trans-(3'''',5''''-difluoro-4''''-difluoromethoxyphenyl)cyclohexyl)ethyl)cyclohexyl)-4E- heptene
318. 8-(4'-trans-(2''-(4'''-trans-(3'''',5''''-difluoro-4''''-difluoromethoxyphenyl)cyclohexyl)ethyl)cyclohexyl)-3m-octene
319. 8-(4'-trans-(2''-(4'''-trans-(3'''',5''''-difluoro-4''''-difluoromethoxyphenyl)cyclohexyl)ethyl)cyclohexyl)-4 E-octene
320. 9-(4'-trans-(2''-(4'''-trans-(3'''',5''''-difluoro-4''''-difluoromethoxyphenyl)cyclohexyl)ethyl)cyclohexyl)-4E-nonene Example 7

Preparation of 2-(4'-trans-(4''-trans-(2'''-(3'''',4'''',5''''-trifluorophenyl)ethyl)cyclohexyl)cyclohexyl)ethene (Compound No. 321)

(1) A suspension of 3,4,5-trifluorobenzyltriphenylphosphonium bromide (51.5 g) in THF (100 ml) was stirred in a nitrogen gas stream, followed by adding sodium methoxide (6.2 g) little by little at room temperature, stirring the reaction solution at room temperature for one hour, dropwise adding a solution of 4-(4'-formylcyclohexyl)cyclohexanone (20 g) in THF(50 ml), stirring the mixture at room temperature for 2 hours, adding to water (500 ml), extracting with ethyl acetate (500 ml), washing the organic layer with water, drying over anhydrous MgSO4, and concentrating the solvent under reduced pressure, to obtain, 4-(4'-trans-(2''-(3''',4''',5'''-trifluorophenyl)ethenyl)cyclohexyl)cyclohexanone (22.5 g).

(2) 4-(4'-trans-(2''-(3''',4''',5'''-trifluorophenyl)ethenyl)cyclohexyl)cyclohexanone (22.5 g) was dissolved in ethanol (250 ml), followed by adding Pd/C (5% ) (5 g), stirring the mixture, hydrogenating in a hydrogen gas atmosphere till completion of absorption of a hydrogen gas, filtering off the catalyst after completion of the reaction, and concentrating the solvent under reduced pressure, to obtain 4-(4'-trans-(2''-(3''',4''',5'''-trifluorophenyl)ethyl)cyclohexyl)cyclohexanone (20.4 g).

(3) A suspension of methoxymethyltriphenylphosphonium chloride (23 g) in THF (50 ml) was stirred in a nitrogen gas stream, followed by cooling it down to 0° C., adding potassium-t-butoxide (8.2 g) little by little, stirring the reaction solution at room temperature for one hour, dropwise adding a solution of 4-(4'-trans-(2''-(3''',4''',5'''-trifluorophenyl)ethyl)cyclohexyl)cyclohexanone(20.4 g) in THF (100 ml), raising the temperature of the reaction mixture up to room temperature, further stirring for 2 hours, pouring into water (250 ml) after completion of the reaction, extracting with ethyl acetate (250 ml), drying the organic layer over anhydrous MgSO4, concentrating under reduced pressure, and carrying out chromatography treatment on silica gel with ethyl acetate/heptane (1:5), to obtain 4-(4'-trans-(2''-(3''',4''',5'''-trifluorophenyl)ethyl)cyclohexyl)methoxymethylenecyclohexane (15.6 g).

(4) THF (30 ml) and 2N hydrochloric acid (30 ml) were added to 4-(4'-trans-(2'-(3''',4''',5'''-trifluorophenyl)ethyl)cyclohexyl)methoxymethylenecyclohexane (15.6 g), followed by heating the mixture under reflux with stirring for 2 hours, adding to water (100 ml) after completion of the reaction, extracting with ethyl acetate (100 ml), drying the organic layer over anhydrous MgSO4, and concentrating under reduced pressure, to obtain 4 (4'-(2''-(3''',4''',5'''-trifluorophenyl)ethyl)cyclohexyl)cyclohexanecarbaldehyde (13.7 g).

(5) A suspension of methyltriphenylphosphonium bromide (15.2 g) in THF (50 ml) was stirred in a nitrogen gas stream, followed by adding potassium-t-butoxide (5.3 g) little by little while cooling at 0° C., stirring the reaction solution at room temperature for one hour, dropwise adding a solution of 4-(4'-trans-(2''-(3''',4''',5'''-trifluorophenyl)ethyl)-cyclohexyl)cyclohexanecarbaldehyde (13.7 g) in THF (50 ml), raising the temperature of the reaction mixture up to room temperature, further stirring for 2 hours, adding to water (100 ml) after completion of the reaction, extracting with ethyl acetate (100 ml), drying the organic layer over anhydrous MgSO4, concentrating under reduced pressure, carrying out chromatography on silica gel with ethyl acetate/heptane (1:5) and recrystallizing from heptane, to obtain 2-(4′-trans-(4″-trans-(2‴-(3⁗,4⁗,5⁗-trifluorophenyl)ethyl)cyclohexyl)ethene (8.2 g).

The following compounds are prepared according to the above procedure:

322. 3-(4′-trans-(4″-trans-(2‴-(3⁗,4⁗,5⁗-trifluorophenyl)ethyl)cyclohexyl)cyclohexyl)-1-propene
323. 3-(4′-trans-(4″-trans-(2‴-(3⁗,4⁗,5⁗-trifluorophenyl)ethyl)cyclohexyl)cyclohexyl)-2E-propene
324. 4-(4′-trans-(4″-trans-(2‴-(3⁗,4⁗,5⁗-trifluorophenyl)ethyl)cyclohexyl)cyclohexyl)-1-butene
325. 4-(4′-trans-(4″-trans-(2‴-(3⁗,4⁗,5⁗-trifluorophenyl)ethyl)cyclohexyl)cyclohexyl)-2E-butene
326. 4-(4′-trans-(4″-trans-(2‴-(3⁗,4⁗,5⁗-trifluorophenyl)ethyl)cyclohexyl)cyclohexyl)-3E-butene
327. 5-(4′-trans-(4″-trans-(2‴-(3⁗,4⁗,5⁗-trifluorophenyl)ethyl)cyclohexyl)cyclohexyl)-1-pentene
328. 5-(4′-trans-(4″-trans-(2‴-(3⁗,4⁗,5⁗-trifluorophenyl)ethyl)cyclohexyl)cyclohexyl)-2E-pentene
329. 5-(4′-trans-(4″-trans-(2‴-(3⁗,4⁗,5⁗-trifluorophenyl)ethyl)cyclohexyl)cyclohexyl)-3E-pentene
330. 5-(4′-trans-(4″-trans-(2‴-(3⁗,4⁗,5⁗-trifluorophenyl)ethyl)cyclohexyl)cyclohexyl)-4E-pentene
331. 6-(4′-trans-(4″-trans-(2‴-(3⁗,4⁗,5⁗-trifluorophenyl)ethyl)cyclohexyl)cyclohexyl)-1-hexene
332. 6-(4′-trans-(4″-trans-(2‴-(3⁗,4⁗,5⁗-trifluorophenyl)ethyl)cyclohexyl)cyclohexyl)-2E-hexene
333. 6-(4′-trans-(4″-trans-(2‴-(3⁗,4⁗,5⁗-trifluorophenyl)ethyl)cyclohexyl)cyclohexyl)-3E-hexene
334. 6-(4′-trans-(4″-trans-(2‴-(3⁗,4⁗,5⁗-trifluorophenyl)ethyl)cyclohexyl)cyclohexyl)-4E-hexene
335. 7-(4′-trans-(4″-trans-(2‴-(3⁗,4⁗,5⁗-trifluorophenyl)ethyl)cyclohexyl)cyclohexyl)-2E-heptene
336. 7-(4′-trans-(4″-trans-(2‴-(3⁗,4⁗,5⁗-trifluorophenyl)ethyl)cyclohexyl)cyclohexyl)-3E-heptene
337. 7-(4′-trans-(4″-trans-(2‴-(3⁗,4⁗,5⁗-trifluorophenyl)ethyl)cyclohexyl)cyclohexyl)-4E-heptene
338. 8-(4′-trans-(4″-trans-(2‴-(3⁗,4⁗,5⁗-trifluorophenyl)ethyl)cyclohexyl)cyclohexyl)-3E-octene
339. 8-(4′-trans-(4″-trans-(2‴-(3⁗,4⁗,5⁗-trifluorophenyl)ethyl)cyclohexyl)cyclohexyl)-4E-octene
340. 9-(4′-trans-(4″-trans-(2‴-(3⁗,4⁗,5⁗-trifluorophenyl)ethyl)cyclohexyl)cyclohexyl)-4E-nonene
341. 2-(4′-trans-(4″-trans-(2‴-(3⁗,5⁗-difluoro-4⁗-trifluoromethylphenyl)ethyl)cyclohexyl)cyclohexyl)ethene
342. 3-(4′-trans-(4″-trans-(2‴-(3⁗,5⁗-difluoro-4⁗-trifluoromethylphenyl)ethyl)cyclohexyl)cyclohexyl)-2E-propene
343. 3-(4′-trans-(4″-trans-(2‴-(3⁗,5⁗-difluoro-4⁗-trifluoromethylphenyl)ethyl)cyclohexyl)cyclohexyl)-1-propene
344. 4-(4′-trans-(4″-trans-(2‴-(3⁗,5⁗-difluoro-4⁗-trifluoromethylphenyl)ethyl)cyclohexyl)cyclohexyl)-1-butene
345. 4-(4′-trans-(4″-trans-(2‴-(3⁗,5⁗-difluoro-4⁗-trifluoromethylphenyl)ethyl)cyclohexyl)cyclohexyl)-2E-butene
346. 4-(4′-trans-(4″-trans-(2‴-(3⁗,5⁗-difluoro-4⁗-trifluoromethylphenyl)ethyl)cyclohexyl)cyclohexyl)-3E-butene
347. 5-(4′-trans-(4″-trans-(2‴-(3⁗,5⁗-difluoro-4⁗-trifluoromethylphenyl)ethyl)cyclohexyl)cyclohexyl)-1-pentene
348. 5-(4′-trans-(4″-trans-(2‴-(3⁗,5⁗-difluoro-4⁗-trifluoromethyl-phenyl)ethyl)cyclohexyl)cyclohexyl)-2E-pentene
349. 5-(4′-trans-(4″-trans-(2‴-(3⁗,5⁗-difluoro-4⁗-phenyl)ethyl)cyclohexyl)cyclohexyl)-3E-pentene
350. 5-(4′-trans-(4″-trans-(2‴-(3⁗,5⁗-difluoro-4⁗-trifluoromethylphenyl)ethyl)cyclohexyl)cyclohexyl)-4E-pentene
351. 6-(4′-trans-(4″-trans-(2‴-(3⁗,5⁗-difluoro-4⁗-trifluoromethylphenyl)ethyl)cyclohexyl)cyclohexyl)-1-hexene
352. 6-(4′-trans-(4″-trans-(2‴-(3⁗,5⁗-difluoro-4⁗-trifluoromethylphenyl)ethyl)cyclohexyl)cyclohexyl)-2E-hexene
353. 6-(4′-trans-(4″-trans-(2‴-(3⁗,5⁗-difluoro-4⁗-trifluoromethylphenyl)ethyl)cyclohexyl)cyclohexyl)-3E-hexene
354. 6-(4′-trans-(4″-trans-(2‴-(3⁗,5⁗-difluoro-4⁗-trifluoromethylphenyl)ethyl)cyclohexyl)cyclohexyl)-4E-hexene
355. 7-(4′-trans-(4″-trans-(2‴-(3⁗,5⁗-difluoro-4⁗-trifluoromethyl)ethyl)cyclohexyl)cyclohexyl)-2E-heptene
356. 7-(4′-trans-(4″-trans-(2‴-(3⁗,5⁗-difluoro-4⁗-trifluoromethylphenyl)ethyl)cyclohexyl)cyclohexyl)-3E-heptene
357. 7-(4′-trans-(4″-trans-(2‴-(3⁗,5⁗-difluoro-4⁗-trifluoromethylphenyl)ethyl)cyclohexyl)cyclohexyl)-4E-heptene
358. 8-(4′-trans-(4″-trans-(2‴-(3⁗,5⁗-difluoro-4⁗-trifluoromethylphenyl)ethyl)cyclohexyl)cyclohexyl)-3E-octene
359. 8-(4′-trans-(4″-trans-(2‴-(3⁗,5⁗-difluoro-4⁗-trifluoromethylphenyl)ethyl)cyclohexyl)cyclohexyl)-4E-octene
360. 9-(4′-trans-(4″-trans-(2‴-(3⁗,5⁗-difluoro-4⁗-trifluoromethylphenyl)ethyl)cyclohexyl)cyclohexyl)-4E-nonene
361. 2-(4′-trans-(4″-trans-(2‴-(3⁗,5⁗-difluoro-4⁗-trifluoromethoxy)ethyl)cyclohexyl)cyclohexyl)ethene
362. 3-(4′-trans-(4″-trans-(2‴-(3⁗,5⁗-difluoro-4⁗-trifluoromethoxyphenyl)ethyl)cyclohexyl)cyclohexyl)-2E-propene
363. 3-(4′-trans-(4″-trans-(2‴-(3⁗,5⁗-difluoro-4⁗-trifluoromethoxyphenyl)ethyl)cyclohexyl)cyclohexyl)-1-propene
364. 4-(4′-trans-(4″-trans-(2‴-(3⁗,5⁗-difluoro-4⁗-trifluoromethoxyphenyl)ethyl)cyclohexyl)cyclohexyl)-1-butene
365. 4-(4′-trans-(4″-trans-(2‴-(3⁗,5⁗-difluoro-4⁗-trifluoromethoxyphenyl)ethyl)cyclohexyl)cyclohexyl)-2E-butene
366. 4-(4′-trans-(4″-trans-(2‴-(3⁗,5⁗-difluoro-4⁗-trifluoromethoxyphenyl)ethyl)cyclohexyl)cyclohexyl)-3E-butene
367. 5-(4′-trans-(4″-trans-(2‴-(3⁗,5⁗-difluoro-4⁗-trifluoromethoxyphenyl)ethyl)cyclohexyl)cyclohexyl)-1-pentene
368. 5-(4′-trans-(4″-trams-(2‴-(3⁗,5⁗-difluoro-4⁗-trifluoromethoxyphenyl)ethyl)cyclohexyl)cyclohexyl)-2E-pentene
369. 5-(4′-trans-(4″-trans-(2‴-(3⁗,5⁗-difluoro-4⁗-trifluoromethoxyphenyl)ethyl)cyclohexyl)cyclohexyl)-3E-pentene
370. 5-(4′-trans-(4″-trans-(2‴-(3⁗,5⁗-difluoro-4⁗-trifluoromethoxyphenyl)ethyl)cyclohexyl)cyclohexyl)-4E-pentene
371. 6-(4′-trans-(4″-trans-(2‴-(3⁗,5⁗-difluoro-4⁗-trifluoromethoxyphenyl)ethyl)cyclohexyl)cyclohexyl)-1-hexene 372. 6-(4'-trans-(4''-trans-(2'''-(3'''',5''''-difluoro-4''''-trifluoromethoxyphenyl)ethyl)cyclohexyl)cyclohexyl)-2E-hexene
373. 6-(4'-trans-(4''-trans-(2'''-(3'''',5''''-difluoro-4''''-trifluoromethoxyphenyl)ethyl)cyclohexyl)cyclohexyl)-3E-hexene
374. 6-(4'-trans-(4''-trans-(2'''-(3'''',5''''-difluoro-4''''-trifluoromethoxyphenyl)ethyl)cyclohexyl)cyclohexyl)-4E-hexene
375. 7-(4'-trans-(4''-trans-(2'''-(3'''',5''''-difluoro-4''''-trifluoromethoxyphenyl)ethyl)cyclohexyl)cyclohexyl)-2E-heptene
376. 7-(4'-trans-(4''-trans-(2'''-(3'''',5''''-difluoro-4''''-trifluoromethoxyphenyl)ethyl)cyclohexyl)cyclohexyl)-3E-heptene
377. 7-(4'-trans-(4''-trans-(2'''-(3'''',5''''-difluoro-4''''-trifluoromethoxyphenyl)ethyl)cyclohexyl)cyclohexyl)-4E-heptene
378. 8-(4'-trans-(4''-trans-(2'''-(3'''',5''''-difluoro-4''''-trifluoromethoxyphenyl)ethyl)cyclohexyl)cyclohexyl)-3E-octene
379. 8-(4'-trans-(4''-trans-(2'''-(3'''',5''''-difluoro-4''''-trifluoromethoxyphenyl)ethyl)cyclohexyl)cyclohexyl)-4E-octene
380. 9-(4'-trans-(4''-trans-(2'''-(3'''',5''''-difluoro-4''''-trifluoromethoxyphenyl)ethyl)cyclohexyl)cyclohexyl)-4E-nonene
381. 2-(4'-trans-(4''-trans-(2'''-(3'''',5''''-difluoro-4''''-difluoromethoxyphenyl)ethyl)cyclohexyl)cyclohexyl)ethene
382. 3-(4'-trans-(4''-trans-(2'''-(3'''',5''''-difluoro-4''''-difluoromethoxyphenyl)ethyl)cyclohexyl)cyclohexyl)-2E-propene
383. 3-(4'-trans-(4''-trans-(2'''-(3'''',5''''-difluoro-4''''-difluoromethoxyphenyl)ethyl)cyclohexyl)cyclohexyl)-1-propene
384. 4-(4'-trans-(4''-trans-(2'''-(3'''',5''''-difluoro-4''''-difluoromethoxyphenyl)ethyl)cyclohexyl)cyclohexyl)-1-butene
385. 4-(4'-trans-(4''-trans-(2'''-(3'''',5''''-difluoro-4''''-difluoromethoxyphenyl)ethyl)cyclohexyl)cyclohexyl)-2E-butene
386. 4-(4'-trans-(4''-trans-(2'''-(3'''',5''''-difluoro-4''''-difluoromethoxyphenyl)ethyl)cyclohexyl)cyclohexyl)-3E-butene
387. 5-(4'-trans-(4''-trans-(2'''-(3'''',5''''-difluoro-4''''-difluoromethoxyphenyl)ethyl)cyclohexyl)cyclohexyl)-1-pentene
388. 5-(4'-trans-(4''-trans-(2'''-(3'''',5''''-difluoro-4''''-difluoromethoxyphenyl)ethyl)cyclohexyl)cyclohexyl)-2E-pentene
389. 5-(4'-trans-(4''-trans-(2'''-(3'''',5''''-difluoro-4''''-difluoromethoxyphenyl)ethyl)cyclohexyl)cyclohexyl)-3E-pentene
390. 5-(4'-trans-(4''-trans-(2'''-(3'''',5''''-difluoro-4''''-difluoromethoxyphenyl)ethyl)cyclohexyl)cyclohexyl)-4E-pentene
391. 6-(4'-trans-(4''-trans-(2'''-(3'''',5''''-difluoro-4''''-difluoromethoxyphenyl)ethyl)cyclohexyl)cyclohexyl)-1-hexene
392. 6-(4'-trans-(4''-trans-(2'''-(3'''',5''''-difluoro-4''''-difluoromethoxyphenyl)ethyl)cyclohexyl)cyclohexyl)-2E-hexene
393. 6-(4'-trans-(4''-trans-(2'''-(3'''',5''''-difluoro-4''''-difluoromethoxyphenyl)ethyl)cyclohexyl)cyclohexyl)-3E-hexene
394. 6-(4'-trans-(4''-trans-(2'''-(3'''',5''''-difluoro-4''''-difluoromethoxyphenyl)ethyl)cyclohexyl)cyclohexyl)-4E-hexene
395. 7-(4'-trans-(4''-trans-(2'''-(3'''',5''''-difluoro-4''''-difluoromethoxyphenyl)ethyl)cyclohexyl)cyclohexyl)-2E-heptene
396. 7-(4'-trans-(4''-trans-(2'''-(3'''',5''''-difluoro-4''''-difluoromethoxyphenyl)ethyl)cyclohexyl)cyclohexyl)-3E-heptene
397. 7-(4'-trans-(4''-trans-(2'''-(3'''',5''''-difluoro-4''''-difluoromethoxyphenyl)ethyl)cyclohexyl)cyclohexyl)-4E-heptene
398. 8-(4'-trans-(4''-trans-(2'''-(3'''',5''''-difluoro-4''''-difluoromethoxyphenyl)ethyl)cyclohexyl)cyclohexyl)-3E-octene
399. 8-(4'-trans-(4''-trans-(2'''-(3'''',5''''-difluoro-4''''-difluoromethoxyphenyl)ethyl)cyclohexyl)cyclohexyl)-4E-octene
400. 9-(4'-trans-(4''-trans-(2'''-(3'''',5''''-difluoro-4''''-difluoromethoxyphenyl)ethyl)cyclohexyl)cyclohexyl)-4E-nonene Example 8

Preparation of 2-(4'-trans-(3'',4'',5''trifluoro-4'''-biphenyl)cyclohexyl)ethene (Compound No. 401)

(1) 4-(3'',4'',5''-Trifluorophenyl)-3'-dicyclohexen-4-one ethylene acetal (20 g) and DDQ (2,3-dichloro-5,6-dicyanobenzoquinone) (16.7 g) were dissolved in toluene (200 ml), followed by stirring the solution under reflux for 4 hours, filtering off deposited insolubles, washing the organic layer with water, drying over anhydrous MgSO₄, distilling off the solvent under reduced pressure, and purifying the resulting raw product according to column chromatography using silica gel (eluting solvent: ethyl acetate/heptane (1:5), to obtain 4-(3',4',5'-trifluoro-4'-biphenyl)cyclo-hexan-4-one ethylene acetal (13.9 g).

(2) Formic acid (10 g) and toluene (2 ml) were added to 4-(3',4',5'-trifluoro-4''-biphenyl)cyclohexan-4-one ethylene acetal (13.9 g), followed by heating the mixture under reflux with stirring for 2 hours, adding the reaction solution to water (50 ml), extracting with ethyl acetate (50 ml), drying the organic layer over anhydrous MgSO₄ and distilling off the solvent under reduced pressure, to obtain 4-(3',4',5'-trifluoro-4''-biphenyl)cyclohexanone (11.5 g).

(3) A suspension of methoxymethyltriphenylphosphonium chloride (13.6 g) in THF (50 ml) was stirred in a nitrogen gas stream, followed by adding potassium-t-butoxide (48 g) little by little while cooling at 0° C., stirring the reaction solution at room temperature for one hour, dropwise adding a solution of 4-(3',4',5'-trifluoro-4''-biphenyl)cyclohexanone (11.5 g) in THF (50 ml), raising the temperature of the reaction mixture up to room temperature, further stirring for 2 hours, adding to water (100 ml) after completion of the reaction, extracting with ethyl acetate (100 ml), drying the organic layer over anhydrous MgSO₄, concentrating under reduced pressure and carrying out chromatography treatment on silica gel with ethyl acetate/heptane (1:5), to obtain 4-(3',4',5'-trifluoro-4''-biphenyl)methoxymethylenecyclohexane (8.8 g).

(4) THF (50 ml) and 2N hydrochloric acid (50 ml) were added to 4-(3',4',5'-trifluoro-4''-biphenyl)methoxymethylene cyclohexane (8.8 g), followed by heating the mixture under reflux with stirring for 2 hours, adding to water (100 ml) after completion of the reaction, extracting with ethyl acetate (100 ml), drying the organic layer over anhydrous MgSO$_4$ and concentrating under reduced pressure, to obtain 4-(3',4',5'-trifluoro-4''-biphenyl)cyclohexanecarbaldehyde (7.5 g).

(5) A suspension of methyltriphenylphosphonium bromide (9 g) in THF (20 ml) was stirred in a nitrogen gas stream, followed by adding potassium-t-butoxide (3.1 g) little by little while cooling at 0° C., stirring the reaction solution at room temperature for one hour, dropwise adding a solution of 4-(3',4',5'-trifluoro-4''-biphenyl)cyclohexanecarbaldehyde (7.5 g) in THF (50 ml), raising the temperature of the reaction mixture up to room temperature further stirring for 2 hours, adding to water (100 ml) after completion of the reaction, extracting with ethyl acetate (100 ml), drying the organic layer over anhydrous MgSO$_4$, concentrating under reduced pressure, carrying out chromatography treatment on silica gel with ethyl acetate/heptane (1:5), and recrystallizing from heptane, to obtain 2-(4'-trans-(3'',4'',5''-trifluoro-4'''-biphenyl)cyclohexyl)ethene (4.6 g).

The following compounds are prepared according to the above procedure:

Compound No.

402. 3-(4'-trans-(3'',4'',5'-trifluoro-4'''biphenylyl)cyclohexyl)-1-propene
403. 3-(4'-trans-(3'',4'',5''-trifluoro-4'''-biphenylyl)cyclohexyl)-2E-propene
404. 4-(4'-trans-(3'',4'',5''-trifluoro-4'''-biphenylyl)cyclohexyl)-1-butene
405. 4-(4'-trans-(3'',4'',5''-trifluoro-4'''-biphenylyl)cyclohexyl)-2E-butene
406. 4-(4'-trans-(3'',4'',5''-trifluoro-4'''-biphenylyl)cyclohexyl)-3E-butene
407. 5-(4'-trans-(3'',4'',5''-trifluoro-4'''-biphenylyl)cyclohexyl)-1-pentene
408. 5 (4'-trans-(3'',4'',5''-trifluoro-4'''biphenylyl)cyclohexyl)-2E-pentene
409. 5-(4'-trans-(3'',4'',5''-trifluoro-4'''-biphenylyl)cyclohexyl)-3E-pentene
410. 5-(4'-trans-(3'',4'',5''-trifluoro-4'''-biphenylyl)cyclohexyl)-4E-pentene
411. 6-(4'-trans-(3'',4'',5''-trifluoro-4'''-biphenylyl)cyclohexyl)-1-hexene
412. 6-(4'-trans-(3'',4'',5''-trifluoro-4'''-biphenylyl)cyclohexyl)-2E-hexene
413. 6-(4'-trans-(3'',4'',5''-trifluoro-4'''-biphenylyl)cyclohexyl)-3E-hexene
414. 6-(4'-trans-(3'',4'',5''-trifluoro-4'''-biphenylyl)cyclohexyl)-4E-hexene
415. 7-(4'-trans-(3'',4'',5''-trifluoro-4'''-biphenylyl)cyclohexyl)-2E-heptene
416. 7-(4'-trans-(3'',4'',5''-trifluoro-4'''-biphenylyl)cyclohexyl)-3E-heptene
417. 7-(4'-trans-(3'',4'',5''-trifluoro-4'''-biphenylyl)cyclohexyl)-4E-heptene
418. 8-(4'-trans-(3'',4'',5''-trifluoro-4'''-biphenylyl)cyclohexyl)-3E-octene
419. 8-(4'-trans-(3'',4'',5''-trifluoro-4'''-biphenylyl)cyclohexyl)-4E-octene
420. 9-(4'-trans-(3'',4'',5''-trifluoro-4'''-biphenylyl)cyclohexyl)-4E-nonene
421. 2-(4'-trans-(3'',5''-difluoro-4''-trifluoromethyl-4'''-biphenylyl)cyclohexyl)ethene
422. 3-(4'-trans-(3'',5''-difluoro-4''-trifluoromethyl-4'''-biphenylyl)cyclohexyl)-2E-propene
423. 3-(4'-trans-(3'',5''-difluoro-4''-trifluoromethyl-4'''-biphenylyl)cyclohexyl)-1-propene
424. 4-(4'-trans-(3'',5''-difluoro-4''-trifluoromethyl-4'''-biphenylyl)cyclohexyl)-1-butene
425. 4-(4'-trans-(3'',5''-difluoro-4''-trifluoromethyl-4'''-biphenylyl)cyclohexyl)-2E-butene
426. 4-(4'-trans-(3'',5''-difluoro-4''-trifluoromethyl-4'''-biphenylyl)cyclohexyl)-3E-butene
427. 5-(4'-trans-(3'',5''-difluoro-4''-trifluoromethyl-4'''-biphenylyl)cyclohexyl)-1-pentene
428. 5-(4'-trans-(3'',5''-difluoro-4''-trifluoromethyl-4'''-biphenylyl)cyclohexyl)-2E-pentene
429. 5-(4'-trans-(3'',5''-difluoro-4''-trifluoromethyl-4'''-biphenylyl)cyclohexyl)-3E-pentene
430. 5-(4'-trans-(3'',5''-difluoro-4''-trifluoromethyl-4'''-biphenylyl)cyclohexyl)-4E-pentene
431. 6-(4'-trans-(3'',5''-difluoro-4''-trifluoromethyl-4'''-biphenylyl)cyclohexyl)-1-hexene
432. 6-(4'-trans-(3'',5''-difluoro-4''-trifluoromethyl-4'''-biphenylyl)cyclohexyl)-2E-hexene
433. 6-(4'-trans-(3'',5''-difluoro-4''-trifluoromethyl-4'''-biphenylyl)cyclohexyl)-3E-hexene
434. 6-(4'-trans-(3'',5''-difluoro-4''-trifluoromethyl-4'''-biphenylyl)cyclohexyl)-4E-hexene
435. 7-(4'-trans-(3'',5''-difluoro-4''-trifluoromethyl-4'''-biphenylyl)cyclohexyl)-2E-heptene
436. 7-(4'-trans-(3'',5''-difluoro-4''-trifluoromethyl-4'''-biphenylyl)cyclohexyl)-3E-heptene
437. 7-(4'-trans-(3'',5''-difluoro-4''-trifluoromethyl-4'''-biphenylyl)cyclohexyl)-4E-heptene
438. 8-(4'-trans-(3'',5''-difluoro-4''-trifluoromethyl-4'''-biphenylyl)cyclohexyl)-3E-octene
439. 8-(4'-trans-(3'',5''-difluoro-4''-trifluoromethyl-4'''-biphenylyl)cyclohexyl)-4E-octene
440. 9-(4'-trans-(3'',5''-difluoro-4''-trifluoromethyl-4'''-biphenylyl)cyclohexyl)-4E-nonene
441. 2-(4'-trans-(3'',5''-difluoro-4''-trifluoromethoxy-4'''-biphenylyl)cyclohexyl)ethene
442. 3-(4'-trans-(3'',5''-difluoro-4''-trifluoromethoxy-4'''-biphenylyl)cyclohexyl)-2E-propene
443. 3-(4'-trans-(3'',5''-difluoro-4''-trifluoromethoxy-4'''-biphenylyl)cyclohexyl)-1-propene
444. 4-(4'-trans-(3'',5''-difluoro-4''-trifluoromethoxy-4'''-biphenylyl)cyclohexyl)-1-butene
445. 4-(4'-trans-(3'',5''-difluoro-4''-trifluoromethoxy-4'''-biphenylyl)cyclohexyl)-2E-butene
446. 4-(4'-trans-(3'',5''-difluoro-4''-trifluoromethoxy-4'''-biphenylyl)cyclohexyl)-3E-butene
447. 5-(4'-trans-(3'',5''-difluoro-4''-trifluoromethoxy-4'''-biphenylyl)cyclohexyl)-1-pentene
448. 5-(4'-trans-(3'',5''-difluoro-4''-trifluoromethoxy-4'''-biphenylyl)cyclohexyl)-2E-pentene
449. 5-(4'-trans-(3'',5''-difluoro-4''-trifluoromethoxy-4'''-biphenylyl)cyclohexyl)-3E-pentene
450. 5-(4'-trans-(3'',5''-difluoro-4''-trifluoromethoxy-4'''-biphenylyl-cyclohexyl)-4E-pentene
451. 6-(4'-trans-(3'',5''-difluoro-4''-trifluoromethoxy-4'''-biphenylyl )cyclohexyl)-1-hexene
452. 6-(4'-trans-(3'',5''-difluoro-4''-trifluoromethoxy-4'''-biphenylyl)cyclohexyl)-2E-hexene
453. 6-(4'-trans-(3'',5''-difluoro-4''-trifluoromethoxy-4'''-biphenylyl)cyclohexyl)-3E-hexene
454. 6-(4'-trans-(3'',5''-difluoro-4''-trifluoromethoxy-4'''-biphenylyl)cyclohexyl)-4E-hexene 455. 7-(4'-trans-(3",5"-difluoro-4"-trifluoromethoxy-4'''-biphenylyl)cyclohexyl)-2E-heptene
456. 7-(4'-trans-(3",5"-difluoro-4"-trifluoromethoxy-4'''-biphenylyl)-cyclohexyl)-3E-heptene
457. 7-(4'-trans-(3",5"-difluoro-4"-trifluoromethoxy-4'''-biphenylyl)cyclohexyl)-4E-heptene
458. 8-(4'-trans-(3",5"-difluoro-4"-trifluoromethoxy-4'''-biphenylyl)cyclohexyl)-3E-octene
459. 8-(4'-trans-(3",5"-difluoro-4"-trifluoromethoxy-4'''-biphenylyl)cyclohexyl)-4E-octene
460. 9-(4'-trans-(3",5"-difluoro-4"-trifluoromethoxy-4'''-biphenylyl)cyclohexyl)-4E-nonene
461. 2-(4'-trans-(3",5"-difluoro-4"-difluoromethoxy-4'''-biphenylyl)cyclohexyl)ethene
462. 3-(4'-trans-(3",5"-difluoro-4"-difluoromethoxy-4'''-biphenylyl)cyclohexyl)-2E-propene
463. 3-(4'-trans-(3",5"-difluoro-4"-difluoromethoxy-4'''-biphenylyl)-cyclohexyl)-1-propene
464. 4-(4'-trans-(3",5"-difluoro-4"-difluoromethoxy-4'''-biphenylyl)cyclohexyl) -1-butene
465. 4-(4'-trans-(3",5"-difluoro-4"-difluoromethoxy-4'''-biphenylyl)cyclohexyl)-2E-butene
466. 4-(4'-trans-(3",5"-difluoro-4"-difluoromethoxy-4'''-biphenylyl)cyclohexyl)-3E-butene
467. 5-(4'-trans-(3",5"-difluoro-4"-difluoromethoxy-4'''-biphenylyl)cyclohexyl)-1-pentene
468. 5-(4'-trans-(3",5"-difluoro-4"-difluoromethoxy-4'''-biphenylyl)cyclohexyl)-2E-pentene
469. 5-(4'-trans-(3",5"-difluoro-4"-difluoromethoxy-4'''-biphenylyl)cyclohexyl)-3E-pentene
470. 5-(4'-trans-(3",5"-difluoro-4"-difluoromethoxy-4'''-biphenylyl)cyclohexyl)-4E-pentene
471. 6-(4'-trans-(3",5"-difluoro-4"-difluoromethoxy-4'''-biphenylyl)cyclohexyl)-1-hexene
472. 6-(4'-trans-(3",5"-difluoro-4"-difluoromethoxy-4'''-biphenylyl)cyclohexyl)-2E-hexene
473. 6-(4'-trans-(3",5"-difluoro-4"-difluoromethoxy-4'''-biphenylyl)cyclohexyl)-3E-hexene
474. 6-(4'-trans-(3",5"-difluoro-4"-difluoromethoxy-4'''-biphenylyl)cyclohexyl)-4E-hexene
475. 7-(4'-trans-(3",5"-difluoro-4"-difluoromethoxy-4'''-biphenylyl)cyclohexyl)-2E-heptene
476. 7-(4'-trans-(3",5"-difluoro-4"-difluoromethoxy-4'''-biphenylyl)cyclohexyl)-3E-heptene
477. 7-(4'-trans-(3",5"-difluoro-4"-difluoromethoxy-4'''-biphenylyl)cyclohexyl)-4E-heptene
478. 8-(4'-trans-(3",5"-difluoro-4"-difluoromethoxy-4'''-biphenylyl)cyclohexyl)-3E-octene
479. 8-(4'-trans-(3",5"-difluoro-4"-difluoromethoxy-4'''-biphenylyl)cyclohexyl)-4E-octene
480. 9-(4'-trans-(3",5"-difluoro-4"-difluoromethoxy-4'''-biphenylyl)cyclohexyl)-4E-nonene Example 9

Preparation of 2-(4'-trans-(2"-(3''',4''',5'''-trifluoro-4'''biphenyl)ethyl)cyclohexyl)ethene (Compound No. 481).

(1) Mg (2 g) was suspended in THF (10 ml) in a nitrogen gas stream, followed by dropwise adding a solution of 3,4,5-trifluorobromobenzene (19.0 g) in THF (150 ml), into the suspension, stirring the mixture at room temperature for one hour, dropwise adding a solution of 1,1-ethylenedioxy-4-(2'-(4"-oxocyclohexyl)ethyl)cyclohexane (20 g) in THF (50 ml), stirring the mixture at room temperature for one hour, adding a saturated aqueous solution of NH$_4$Cl(200 ml) after completion of the reaction, extracting with ethyl acetate (500 ml), drying the organic layer over anhydrous MgSO$_4$, and distilling off the solvent under reduced pressure, to obtain 1,1-ethylenedioxy-4-(2'-(4"-hydroxy-4"-(3''',4''',5'''-trifluorophenyl)cyclohexyl)ethylcyclohexane (23.8 g).

(2) p-Toluenesulfonic acidmonohydrate (5 g) was added into a solution of 1,1-ethylenedioxy-4-(2'-(4"-hydroxy-4'''-(3''',4''',5'''-trifluorophenyl)cyclohexyl)ethyl)cyclohexane (23.8 g) in toluene (250 ml), followed by stirring the mixture under reflux for one hour, washing the reaction solution with water (250 ml), drying the organic layer over anhydrous MgSO$_4$ and distilling off the solvent under reduced pressure, to obtain 1,1-ethylenedioxy-4-(2'-(4"-(3''',4''',5'''-trifluorophenyl)-3"-cyclohexenyl)ethyl)cyclohexane (18.2 g).

(3) 1,1-Ethylenedioxy-4-(2'-(4"-(3''',4'41 ,5'''-trifluorophenyl)-3"-cyclohexenyl)ethyl)cyclohexane (18.2 g) and DDQ (14.1 g) were dissolved in toluene (250 ml), followed by stirring the mixture under reflux for 4 hours, filtering off deposited insolubles, washing the organic layer with water, drying over anhydrous MgSO$_4$, distilling off the solvent under reduced pressure, and purifying the resulting raw product according to column chromatography on silica gel (eluent solvent: ethyl acetate/heptane=1/5), to obtain 1,1-ethylenedioxy-4-(2'-(3",4",5"-trifluoro-4'''-biphenyl)ethyl)cyclohexane (12.6 g).

(4) Formic acid (10 g) and toluene (2 ml) were added to 1,1-ethylenedioxy-4-(2'-(3",4",5"-trifluoro-4'''-biphenyl)ethyl)cyclohexane (12.6 followed by heating the mixture under reflux with stirring for 2 hours, adding the reaction solution to water (50 ml), extracting with ethyl acetate (50 ml), drying the organic solvent over anhydrous MgSO$_4$, and distilling off the solvent under reduced pressure, to obtain 4-(2'-(3",4",5"-trifluoro-4'''-biphenyl)ethyl)cyclohexanone (10.0 g).

(5) A suspension of methoxymethyltriphenylphosphonium chloride (11.3 g) in THF (50 ml) was stirred in a nitrogen gas stream, followed by adding potassium-t-butoxide (4.1 g) little by little while cooling at 0° C. stirring the reaction solution at room temperature for one hour, dropwise adding a solution of 4-(2'-(3",4",5"-trifluoro-4'''-biphenyl)ethyl)cyclohexanone (10.0 g) in THF (50 ml), raising the temperature of the reaction mixture up to room temperature, further stirring the mixture for 2 hours, adding to water (100 ml) after completion of the reaction, extracting with ethyl acetate (200 ml), drying the organic layer over anhydrous MgSO$_4$, concentrating under reduced pressure and carrying out chromatography treatment on silica gel with ethyl acetate/heptane (1:5), to obtain 4-(2'-(3",4",5"-trifluoro-4'''-biphenyl)ethyl)methoxymethylenecyclohexane (7.5 g).

(6) THF (50 ml) and 2N hydrochloric acid (50 ml) were added to 4-(2'-(3",4",5"trifluoro-4'''-biphenyl)ethyl)methoxymethylenecyclohexane (7.5 g), followed by heating the mixture under reflux with stirring for 2 hours, adding to water (100 ml) after completion of the reaction, extracting with ethyl acetate (100 ml), drying the organic layer over anhydrous MgSO$_4$, and concentrating under reduced pressure, to obtain 4-(2'-(3",4",5"-trifluoro-4'''-biphenyl)ethyl)cyclohexylcarbaldehyde (5.8 g).

(7) A suspension of methyltriphenylphosphonium bromide (7.2 g) in THF (20 ml) was stirred in a nitrogen gas stream, followed by adding potassium-t-butoxide (1.6 g) little by little while cooling at 0° C., stirring the resulting reaction solution at room temperature for one hour, dropwise adding a solution of 4-(2'(3'',4''',5''-trifluoro-4'''-biphenyl)ethyl)cyclohexanecarbaldehyde (5.8 g) in THF (50 ml), raising the temperature of the reaction mixture up to room temperature, further stirring for 2 hours, adding to water (100 ml) after completion of the reaction, extracting with ethyl acetate (100 ml), drying the organic layer over anhydrous MgSO4, concentrating under reduced pressure, carrying out chromatography treatment on silica gel with ethyl acetate/heptane (1:5) and recrystallizing from heptane, to obtain 2-(4'-trans-(2''-(3''',4''',5'''-trifluoro-4'''biphenyl)ethyl)cyclohexyl)ethene (3.5 g).

The following compounds are prepared by repeating the above-mentioned carbon number-increasing reactions:

482. 3-(4'-trans-(2''-(3''',4''',5'''-trifluoro-4'''-biphenylyl)ethyl)cyclohexyl)-1-propene
483. 3-(4'-trans-(2''-(3''',4''',5'''-trifluoro-4'''-biphenylyl)ethyl)cyclohexyl)-2E-propene
484. 4-(4'-trans-(2''-(3''',4''',5'''-trifluoro-4'''-biphenylyl)ethyl)cyclohexyl)-1-butene
485. 4-(4'-trans-(2''-(3''',4''',5'''-trifluoro-4'''-biphenylyl)ethyl)cyclohexyl)-2E-butene
486. 4-(4'-trans-(2''-(3''',4''',5'''-trifluoro-4'''-biphenylyl)ethyl)cyclohexyl)-3E -butene
487. 5-(4'-trans-(2''-(3''',4''',5'''-trifluoro-4'''-biphenylyl)ethyl)cyclohexyl)-1-pentene
488. 5-(4'-trans-(2''-(3''',4''',5'''-trifluoro-4'''-biphenylyl)ethyl)cyclohexyl)-2E-pentene
489. 5-(4'-trans-(2''-(3''',4''',5'''-trifluoro-4'''-biphenylyl)ethyl)cyclohexyl)-3E-pentene
490. 5-(4'-trans-(2''-(3''',4''',5'''-trifluoro-4'''-biphenylyl)ethyl)cyclohexyl)-4E-pentene
491. 6-(4'-trans-(2''-(3''',4''',5'''-trifluoro-4'''-biphenylyl)ethyl)cyclohexyl)-1-hexene
492. 6-(4'-trans-(2''-(3''',4''',5'''-trifluoro-4'''-biphenylyl)ethyl)cyclohexyl)-2E-hexene
493. 6-(4'-trans-(2''-(3''',4''',5'''-trifluoro-4'''-biphenylyl)ethyl)cyclohexyl)-3E-hexene
494. 6-(4'-trans-(2''-(3''',4''',5'''-trifluoro-4'''-biphenylyl)ethyl)cyclohexyl)-4E-hexene
495. 7-(4'-trans-(2''-(3''',4''',5'''-trifluoro-4'''-biphenylyl)ethyl)cyclohexyl)-2E-heptene
496. 7-(4'-trans-(2''-(3''',4''',5'''-trifluoro-4'''-biphenylyl)ethyl)cyclohexyl)-3E-heptene
497. 7-(4'-trans-(2''-(3''',4''',5'''-trifluoro-4'''-biphenylyl)ethyl)-4E-heptene
498. 8-(4'-trans-(2''-(3''',4''',5'''-trifluoro-4'''-biphenylyl)ethyl)cyclohexyl)-3E-octene
499. 8-(4'-trans-(2''-(3''',4''',5'''-trifluoro-4'''-biphenylyl)ethyl)cyclohexyl)-4E-octene
500. 9-(4'-trans-(2''-(3''',4''',5'''-trifluoro-4'''-biphenylyl)ethyl)cyclohexyl)-4E -nonene
501. 2-(4'-trans-(2''-(3''',5'''-difluoro-4'''-trifluoromethyl-4'''-biphenylyl)ethyl)cyclohexyl)ethene
502. 3-(4'-trans-(2''-(3''',5'''-difluoro-4'''-trifluoromethyl-4'''-biphenylyl)ethyl)cyclohexyl)-2E-propene
503. 3-(4'-trans-(2''-(3''',5'''-difluoro-4'''-trifluoromethyl-4'''-biphenylyl)ethyl)cyclohexyl)-1-propane
504. 4-(4'-trans-(2''-(3''',5'''-difluoro-4'''-trifluoromethyl-4'''-biphenylyl)ethyl)cyclohexyl)1-butene
505. 4-(4'-trans-(2''-(3''',5'''-difluoro-4'''-trifluoromethyl-4'''-biphenylyl)ethyl)cyclohexyl)-2E-butene
506. 4-(4'-trans-(2''-(3''',5'''-difluoro-4'''-trifluoromethyl-4'''-biphenylyl)ethyl)cyclohexyl)-3E-butene
507. 5-(4'-trans-(2''-(3''',5'''-difluoro-4'''-trifluoromethyl-4'''-biphenylyl)ethyl)cyclohexyl)-1-pentene
508. 5-(4'-trans-(2''-(3''',5'''-difluoro-4'''-trifluoromethyl-4'''-biphenylyl)ethyl)cyclohexyl)-2E-pentene
509. 5-(4'-trans-(2''-(3''',5'''-difluoro-4'''-trifluoromethyl-4'''-biphenylyl)ethyl)cyclohexyl)-3E-pentene
510. 5-(4'-trans-(2''-(3''',5'''-difluoro-4'''-trifluoromethyl-4'''-biphenylyl)ethyl)cyclohexyl)-4E-pentene
511. 6-(4'-trans-(2''-(3''',5'''-difluoro-4'''-trifluoromethyl-4'''-biphenylyl)ethyl)cyclohexyl)-1-hexene
512. 6-(4'-trans-(2''-(3''',5'''-difluoro-4'''-trifluoromethyl-4'''-biphenylyl)ethyl)cyclohexyl)-2E-hexene
513. 6-(4'-trans-(2''-(3''',5'''-difluoro-4'''-trifluoromethyl-4'''-biphenylyl)ethyl)cyclohexyl)-3E-hexene
514. 6-(4'-trans-(2''-(3''',5'''-difluoro-4'''-trifluoromethyl-4'''-biphenylyl)ethyl)cyclohexyl)-4E-hexene
515. 7-(4'-trans-(2''-(3''',5'''-difluoro-4'''-trifluoromethyl-4'''-biphenylyl)ethyl)cyclohexyl)-2E-heptene
516. 7-(4'-trans-(2''-(3''',5'''-difluoro-4'''-trifluoromethyl-4'''-biphenylyl)ethyl)cyclohexyl)-3E-heptene
517. 7-(4'-trans-(2''-(3''',5'''-difluoro-4'''-trifluoromethyl-4'''-biphenylyl)ethyl)cyclohexyl)-4E-heptene
518. 8-(4'-trans-(2''-(3''',5'''-difluoro-4'''-trifluoromethyl-4'''-biphenylyl)ethyl)cyclohexyl)-3E-octene
519. 8-(4'-trans-(2''-(3''',5'''-difluoro-4'''-trifluoromethyl-4'''-biphenylyl)ethyl)cyclohexyl)-4E-octene
520. 9-(4'-trans-(2''-(3''',5'''-difluoro-4'''-trifluoromethyl-4'''-biphenylyl)ethyl)cyclohexyl)-4E-nonene
521. 2-(4'-trans-(2''-(3''',5'''-difluoro-4'''-trifluoromethoxy-4'''-biphenylyl)ethyl)cyclohexyl)ethene
522. 3-(4'-trans-(2''-(3''',5'''-difluoro-4'''-trifluoromethoxy-4'''-biphenylyl)ethyl)cyclohexyl)-2E-propene
523. 3-(4'-trans-(2''-(3''',5'''-difluoro-4'''-trifluoromethoxy-4'''-biphenylyl)ethyl)cyclohexyl)-1-propene
524. 4-(4'-trans-(2''-(3''',5'''-difluoro-4'''-trifluoromethoxy-4'''-biphenylyl)ethyl)cyclohexyl)-1-butene
525. 4-(4'-trans-(2''-(3''',5'''-difluoro-4'''-trifluoromethoxy-4'''-biphenylyl)ethyl)cyclohexyl)-2E -butene
526. 4-(4'-trans-(2''-(3''',5'''-difluoro-4'''-trifluoromethoxy-4'''-biphenylyl)ethyl)cyclohexyl)-3E-butene
527. 5-(4'-trans-(2''-(3''',5'''-difluoro-4'''-trifluoromethoxy-4'''-biphenylyl)ethyl)cyclohexyl)-1-pentene
528. 5-(4'-trans-(2''-(3''',5'''-difluoro-4'''-trifluoromethoxy-4'''-biphenylyl)ethyl)cyclohexyl)-2E-pentene
529. 5-(4'-trans-(2''-(3''',5'''-difluoro-4'''-trifluoromethoxy-4'''-biphenylyl)ethyl)cyclohexyl)-3E-pentene
530. 5-(4'-trans-(2''-(3''',5'''-difluoro-4'''-trifluoromethoxy-4'''-biphenylyl)ethyl)cyclohexyl)-4E-pentene
531. 6-(4'-trans-(2''-(3''',5'''-difluoro-4'''-trifluoromethoxy-4'''-biphenylyl)ethyl)cyclohexyl)-1-hexene
532. 6-(4'-trans-(2''-(3''',5'''-difluoro-4'''-trifluoromethoxy-4'''-biphenylyl)ethyl)cyclohexyl)-2E-hexene
533. 6-(4'-trans-(2''-(3''',5'''-difluoro-4'''-trifluoromethoxy-4'''-biphenylyl)ethyl)cyclohexyl)-3E-hexene
534. 6-(4'-trans-(2''-(3''',5'''-difluoro-4'''-trifluoromethoxy-4'-biphenylyl)ethyl)cyclohexyl)-4E-hexene
535. 7-(4'-trans-(2''-(3''',5'''-difluoro-4'''-trifluoromethoxy-4'''-biphenylyl)ethyl)cyclohexyl)-2E-heptene
536. 7-(4'-trans-(2''-(3''',5'''-difluoro-4'''-trifluoromethoxy-4'''-biphenylyl)ethyl)cyclohexyl)-3E-heptene
537. 7-(4'-trans-(2''-(3''',5'''-difluoro-4'''-trifluoromethoxy-4'''-biphenylyl)ethyl)cyclohexyl)-4E-heptene 538. 8-(4'-trans-(2''-(3''',5'''-difluoro-4'''-trifluoromethoxy-4'''-biphenylyl)ethyl)cyclohexyl)-3E-octene
539. 8-(4'-trans-(2''-(3''',5'''-difluoro-4'''-trifluoromethoxy-4'-biphenylyl)ethyl)cyclohexyl)-4E-octene
540. 9-(4'-trans-(2''-(3''',5'''-difluoro-4'''-trifluoromethoxy-4'''-biphenylyl)ethyl)cyclohexyl)-4E-nonene
541. 2-(4'-trans-(2''-(3''',5'''-difluoro-4'''-difluoromethoxy-4'''-biphenylyl)ethyl)cyclohexyl)ethene
542. 3-(4'-trans-(2''-(3''',5'''-difluoro-4'''-difluoromethoxy-4'''-biphenylyl)ethyl)cyclohexyl)-2E-propene
543. 3-(4'-trans-(2''-(3''',5'''-difluoro-4'''-difluoromethoxy-4'''-biphenylyl)ethyl)cyclohexyl)-1-propene
544. 4-(4'-trans-(2''-(3''',5'''-difluoro-4'''-difluoromethoxy-4'''-biphenylyl)ethyl)cyclohexyl)-1-butene
545. 4-(4'-trans-(2''-(3''',5'''-difluoro-4'''-difluoromethoxy-4'''-biphenylyl)ethyl)cyclohexyl)-2E-butene
546. 4-(4'-trans-(2''-(3''',5'''-difluoro-4'''-difluoromethoxy-4'''-biphenylyl)ethyl)cyclohexyl)-3E-butene
547. 5-(4'-trans-(2''-(3''',5'''-difluoro-4'''-difluoromethoxy-4'''-biphenylyl)ethyl)cyclohexyl)-1-pentene
548. 5-(4'-trans-(2''-(3''',5'''-difluoro-4'''-difluoromethoxy-4'''-biphenylyl)ethyl)cyclohexyl)-2E-pentene
549. 5-(4'-trans-(2''-(3''',5'''-difluoro-4'''-difluoromethoxy-4'''-biphenylyl)ethyl)cyclohexyl)-3E-pentene
550. 5-(4'-trans-(2''-(3''',5'''-difluoro-4'''-difluoromethoxy-4'''-biphenylyl)ethyl)cyclohexyl)-4E-pentene
551. 6-(4'-trans-(2''-(3''',5'''-difluoro-4'''-difluoromethoxy-4'''-biphenylyl)ethyl)cyclohexyl)-1-hexene
552. 6-(4'-trans-(2''-(3''',5'''-difluoro-4'''-difluoromethoxy-4'''-biphenylyl)ethyl)cyclohexyl)-2E-hexene
553. 6-(4'-trans-(2''-(3''',5'''-difluoro-4'''-difluoromethoxy-4 '-biphenylyl)ethyl)cyclohexyl)-3E-hexene
554. 6-(4'-trans-(2''-(3''',5'''-difluoro-4'''-difluoromethoxy-4 '-biphenylyl)ethyl)cyclohexyl)-4E-hexene
555. 7-(4'-trans-(2''-(3''',5'''-difluoro-4'''-difluoromethoxy-4'''-biphenylyl)ethyl)cyclohexyl)-2E-heptene
556. 7-(4'-trans-(2''-(3''',5'''-difluoro-4'''-difluoromethoxy-4'''-biphenylyl)ethyl)cyclohexyl)-3E-heptene
557. 7-(4'-trans-(2''-(3''',5'''-difluoro-4'''-difluoromethoxy-4'''-biphenylyl)ethyl)cyclohexyl)-4E-heptene
558. 8-(4'-trans-(2''-(3''',5'''-difluoro-4'''-difluoromethoxy-4'''-biphenylyl)ethyl)cyclohexyl)-3E-octene
559. 8-(4'-trans-(2''-(3''',5'''-difluoro-4'''-difluoromethoxy-4'''-biphenylyl)ethyl)cyclohexyl)-4E-octene
560. 9-(4'-trans-(2''-(3''',5'''-difluoro-4'''-difluoromethoxy-4'''-biphenylyl)ethyl)cyclohexyl)-4E-nonene Application Example 1

A compound of the present invention (15 parts by weight) shown in Example 1 was added to a composition A consisting of

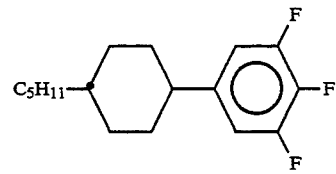

| $C_3H_7$—◯—◯—CN | 25.5 weight parts |
| $C_5H_{11}$—◯—◯—CN | 34.0 weight parts |
| $C_7H_{15}$—◯—◯—CN | 25.5 weight parts and |
| $C_5H_{11}$—◯—◯—◯—CN | 15.0 weight parts |

The resulting liquid crystal composition exhibited an NI point of −95.6° C. when extrapolated, and a viscosity at 20° C. of 2.3 cp. This liquid crystal composition was sealed in a TN cell of 8.7 μm thick, and its threshold voltage was observed to give 1.28 V. Its elastic constant of $K_{33}/K_{11}$, was 1.99 and that of $K_{33}/K_{22}$ was 2.69.

As a comparative example, a comparative compound (B) expressed by the formula,

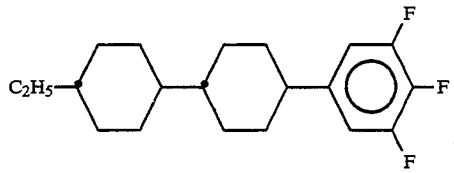

(15 parts by weight) was added to the composition (A) (85 parts by weight). The resulting liquid crystal composition exhibited a NI joint of −59.6° C. when extrapolated, and a viscosity at 20° C. of −1.0 cp. Further, this liquid crystal composition was sealed in a TN cell of 8.7 μm thick, and its threshold voltage was observed to give 1.44 V. Its elastic constant of $K_{33}/K_{11}$ was 1.74 and that of $K_{33}/K_{22}$ was 2.07.

Application Example 2

A compound of the present invention shown in Example 2 (15 parts by weight) was added to the composition A used in Application example 1 (85 parts by weight). The resulting liquid crystal composition exhibited an NI point of −119.6° C. when extrapolated. When the composition was filled in a TN cell of 8.7 μm thick and the threshold voltage was observed to give 1.15 V. The elastic constant of $K_{33}/K_{11}$ was 1.77 and that of $K_{33}/K_{22}$ was 2.53.

Application Example 3

A compound of the present invention shown in Example 4 (15 parts by weight) was added to the composition A used in Application example 1. The resulting liquid crystal composition exhibited an NI point of 57.1° C. and a viscosity at 20° C. of 3.1 cp. This liquid crystal composition was filled in a TN cell of 8.7 μm thick and the threshold voltage was observed to give 1.55 V. The elastic constant of $K_{33}/K_{11}$ was 2.00 and that of $K_{33}/K_{22}$ was 2.93.

As a comparative example, a comparative compound (C) expressed by the formula (15 parts by weight) was added to the composition A used in Application example 1 (85 parts by weight). The liquid crystal composition exhibited an NI point of 47.7° C. when extrapolated and a viscosity at 20° C. of 30.3 cp. This liquid crystal composition was filled in a TN cell of 8.8 μm thick and the threshold voltage was observed to give 1.48 V, The elastic constant of $K_{33}/K_{11}$ was 2.11 and that of $K_{33}/K_{22}$ was 2.86.

Application Example 4

A compound of the present invention shown in Example 3 (15 parts by weight) was added to the composition A used in Application example 1 (85 parts by weight). The resulting liquid crystal composition exhibited an NI point of −133.6° C. when extrapolated, Further, this liquid crystal composition was filled in a TN cell of 8.7 μm thick and the threshold voltage was observed to give 1.00 V.

Application Example 5

A compound of the present invention shown as compound No. 84 (15 parts by weight) was added to the composition A used in Application example 1 (85 parts by weight). The resulting liquid crystal composition exhibited an NI point of 79.1° C. when extrapolated and a viscosity at 20° C. of 29.0 cp. This liquid crystal composition was filled in a TN cell of 8.6 μm thick and the threshold voltage was observed to give 1.63 V.

Effectiveness of the Invention

The compound provided by the present invention has a low viscosity and when the compound is added, it is possible to lower the threshold voltage of the resulting display element.

What we claim is:

1. A cyclohexane derivative expressed by the formula (I)

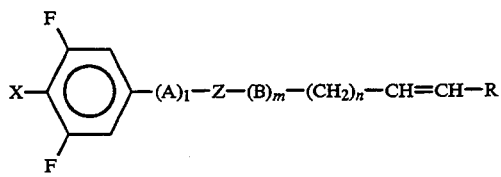

wherein X represents a fluorine atom, a trifluoromethyl group, a trifluoromethoxy group or a difluoromethoxy group, —A— represents 1,4-cyclohexylene or 1,4-phenylene, —B— represents 1,4-cyclohexylene, l represents 0, 1 or 2, m represents 0, 1 or 2, and l+m=1 or 2, Z represents —CH$_2$CH$_2$— or a single bond, n represents an integer of 0 to 4, R represents a hydrogen atom or a linear alkyl group of 1 to 7 carbon atoms, and when R represents an alkyl group, the double bond has a trans-configuration; excluding 5-(4'-trans-(3",4",5"-trifluorophenyl)cyclohexyl)-2E-pentene.

2. A cyclohexane derivative according to claim 1, wherein —A— represents 1,4-cyclohexylene, l represents 1, m represents 0 and Z represents a single bond.

3. A cyclohexane derivative according to claim 1, wherein —A— represents 1,4-cyclohexylene, l represents 2, m represents 0 and Z represents a single bond.

4. A cyclohexane derivative according to claim 1, wherein l represents 0, m represents 1 and Z represents —CH$_2$CH$_2$—.

5. A cyclohexane derivative according to claim 1, wherein —A— represents 1,4-cyclohexylene, l represents 1, m represents 1 and Z represents —CH$_2$CH$_2$—.

6. A cyclohexane derivative according to claim 1, wherein —B— represents 1,4-cyclohexylene, l represents 0, m represents 2 and Z represents —CH$_2$CH$_2$—.

7. A cyclohexane derivative according to claim 1, wherein —A— represents 1,4-phenylene, l represents 1, m represents 0 and Z represents a single bond.

8. A cyclohexane derivative according to claim 1, wherein —A— represents 1,4-phenylene, l represents 1, m represents 1 and Z represents —CH$_2$CH$_2$—.

9. A liquid crystal composition comprising at least one liquid crystalline compound and at least one cyclohexane derivative expressed by the formula (I)

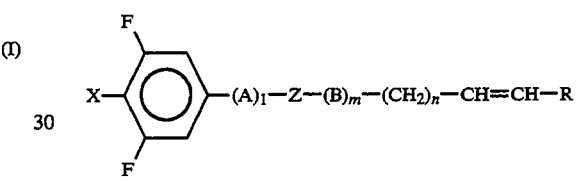

wherein X represents a fluorine atom, a trifluoromethyl group, a trifluoromethoxy group or a difluoromethoxy group, —A— represents 1,4-cyclohexylene or 1,4-phenylene, —B— represents 1,4-cyclohexylene, l represents 0, 1 or 2, m represents 0, 1 or 2, and l+m=1 or 2, Z represents —CH$_2$CH$_2$— or a single bond, n represents an integer of 0 to 4, R represents a hydrogen atom or a linear alkyl group of 1 to 7 carbon atoms, and when R represents an alkyl group, the double bond has a trans-configuration; excluding 5-(4'-trans-(3",4",5"-trifluorophenyl)cyclohexyl)-2E-pentene.

* * * * *